(12) United States Patent
Haesslein et al.

(10) Patent No.: US 6,583,119 B2
(45) Date of Patent: Jun. 24, 2003

(54) AROMATIC AMIDES, PREPARATION METHOD AND APPLICATION AS MEDICINES

(75) Inventors: Jean-Luc Haesslein, Courtry (FR); Michel Klich, Villemomble (FR); Patrick Laurin, Montreuil (FR); Branislav Musicki, Paris (FR); Anne-Marie Periers, Moussy-le-Neuf (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 10/162,852

(22) Filed: Jun. 5, 2002

(65) Prior Publication Data

US 2003/0060609 A1 Mar. 27, 2003

Related U.S. Application Data

(62) Division of application No. 09/600,053, filed as application No. PCT/FR99/00014 on Jan. 7, 1999, now Pat. No. 6,420,538.

(30) Foreign Application Priority Data

Jan. 8, 1998 (FR) .............................................. 98 00116
Oct. 15, 1998 (FR) .............................................. 98 12936

(51) Int. Cl.[7] .......................... A61K 31/70; C07H 15/00
(52) U.S. Cl. .............................................. 514/27; 536/8
(58) Field of Search ................................. 536/8; 514/27

(56) References Cited

U.S. PATENT DOCUMENTS 6,420,538 B1 * 7/2002 Haesslein et al. ............... 536/8

* cited by examiner

*Primary Examiner*—Elli Peselev
(74) *Attorney, Agent, or Firm*—Muserlian, Lucas and Mercanti

(57) ABSTRACT

The invention relates to aromatic amides of formula

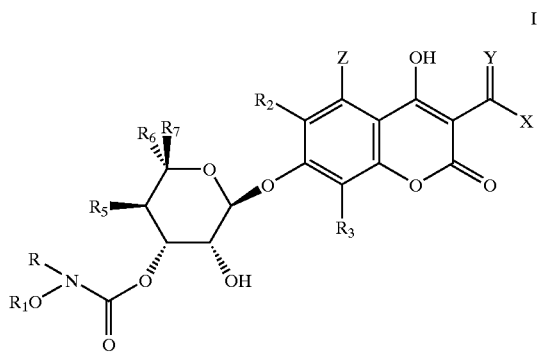

wherein the various substituents are defined as set forth in the specification which have antibiotic activity.

17 Claims, No Drawings

AROMATIC AMIDES, PREPARATION METHOD AND APPLICATION AS MEDICINES

This application is a division of U.S. patent application Ser. No. 09/600,053 filed Aug. 30, 2000, now U.S. Pat. No. 6,420,538 B1 which is a 371 of PCT/FR99/00014 filed Jan. 7, 1999.

The present invention relates to new aromatic amides, their preparation process and their use as medicaments.

A subject of the invention is the compounds of formula (I):

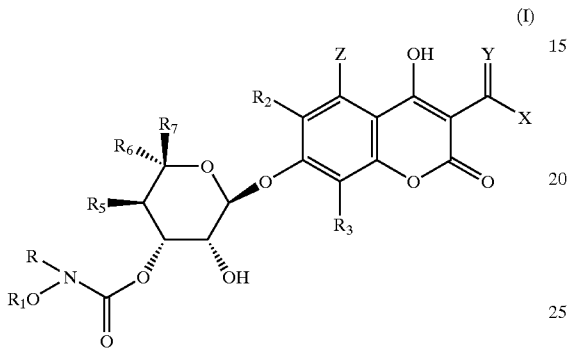

in which:

Y represents an oxygen atom, or an N-Nalk$_1$ or NOalk$_2$ radical in which alk$_1$ and alk$_2$ represent an alkyl radical, containing up to to 12 carbon atoms optionally interrupted by one or more oxygen, sulphur or nitrogen atoms, optionally substituted by one or more halogen atoms, by an aryl radical optionally substituted by one or more halogen atoms, by a heterocyclic radical, by one or more

radicals in which Ra and Rb identical or different from one another represent a hydrogen atom, an optionally substituted alkyl radical containing up to 8 carbon atoms, or Ra and Rb form together with the nitrogene atom to which they are joined a heterocycle which can contain in addition another heteroatom chosen from oxygen, sulphur or nitrogen, X represents a hydrogen atom, a hydroxyl radical, a linear, branched or cyclic alkyl, alkenyl or alkynyl radical optionally interrupted by one or more oxygen, sulphur and or nitrogen atoms, containing up to 12 carbon atoms, optionally substituted by one or more halogen atoms, by a heterocyclic radical, one or more free or esterified OH, C≡N, NO$_2$,

radicals in which Ra and Rb, identical or different, represent a hydrogen atom, an alkyl radical containing up to 8 carbon atoms, or Ra and Rb form together with the nitroaen atom to which they are linked a hetero-cycle optionally containing another heteroatom chosen from nitrogen, sulphur or oxygen, or X represents an alkoxy radical or a

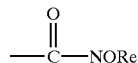

radical in which Re represents an alkyl radical containing up to 8 carbon atoms, optionally substituted by one or more of the substituents indicated above, or X represents an NRcRd radical in which Rc and Rd identical or different, represent a hydrogen atom or an alkyl radical containing up to 12 carbon atoms, optionally substituted by one or more of the substituants indicated above, or Rc and Rd form together with the nitrogen atom to which they are linked a heterocycle optionally containing another heteroatom chosen from nitrogen, sulphur or oxygen, Z represents a hydrogen or halogen atom or a free, etherified or esterified OH radical, R$_2$ represents a hydrogen or halogen atom, R$_3$ represents a hydrogen atom, an alkyl radical containing up to 8 carbon atoms or a halogen atom, R represents a hydrogen atom or an alkyl radical containing up to 4 carbon atoms, R$_1$ represents a hydrogen atom, a linear, branched or cyclic alkyl, alkenyl or alkynyl radical containing up to 8 carbon atoms, optionally substituted by one or more halogen atoms, a C≡N radical, an aryl radical containing up to 14 carbon atoms, R$_5$ represents a hydrogen atom, an O-alkyl radical containing up to 4 carbon atoms, either R$_6$ represents an alkyl or CH$_2$—O-alkyl radical, in which alkyl represents an alkyl radical containing up to 8 carbon atoms, R$_7$ represents a hydrogen atom or an alkyl radical containing up to 8 carbon atoms, or R$_6$ and R$_7$ form together with the carbon atom which they carry a ring containing up to 8 carson atoms, as well as the salts of the compound of formula (I), when the compounds of formula (I) have a basic function.

As examples of salts there can also be mentioned the salts formed with the following acids: acetic, propionic, trifluoroacetic, maleic, tartaric, methanesulphonic, benzenesulphonic, paratoluenesulphonic, hydrochloric, hydrobromic, hydroiodic, sulphuric, phosphoric and especially stearic, ethylsuccinic or laurylsulphonic acids.

In the definition of the substituents:

the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, cyclobutyl, cyclopentyl or cyclohexyl radical, the halogen is preferably fluorine or chlorine, or bromine, the aryl radical is preferably the phenyl radical, the heterocyclic radical is preferably the pyrrolyl, pyrrolidinyl, pyridyl, pyrazinyl, pyrimidyl, piperidinyl, piperazinyl, quinuclidinyl, oxazolyl, isoxazolyl, morpholinyl, indolyl, imidazolyl, benzimidazolyl, triazolyl, thiazolyl, azetidinyl, aziridinyl radical.

A more particular subject of the invention is the compounds of formula (I) in which Y represents an oxygen atom, those in which Y represents an NO-alkyl radical in which the alkyl radical contains up to 4 carbon atoms, for example those in which Y represents the NOC$_2$H$_5$ radical.

Among the preferred compounds of the invention there can be mentioned the compounds of formula (I) in which X represents an alkyl radical containing up to 4 carbon atoms and in particular the $CH_3$ radical, or also those in which X represents an $NH_2$ radical, or also those in which X represents the:

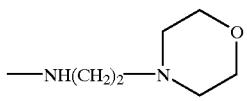

radical.

Among the preferred compounds of the invention, there can be mentioned the compounds of formula (I) in which $R_1$ represents a

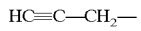

radical those in which R represents a hydrogen atom, or also those in which $R_3$ represents a methyl radical, or also those in which Z represents a hydrogen atom, or also those in which $R_2$ represents a hydrogen atom, or also those in which $R_5$ represents an $OCH_3$ radical, or also those in which $R_6$ represents a methyl radical, or also those in which $R_7$ represents a methyl radical, those in which $R_7$ represents an ethyl radical, those in which $R_6$ and $R_7$ form with the carbon which carries them a cyclopentyl radical.

Among the preferred compounds of the invention, there can be mentioned the compounds whose preparation is given hereafter in the experimental part and, quite particularly the compounds of 1, 2, 3, 4, 5 and 9.

The products of general formula (I) have a very good antibiotic activity on gram$^\oplus$bacteria such as staphylococci, streptococci, pneumococci, enterococci, listeria, anaerobes.

The compounds of the invention can therefore be used as medicaments in the treatment of germ-sensitive infections and in particular, in that of staphylococcia such as staphylococcal septicaemias, malignant staphylococcia of the face or skin, pyodermitis, septic or suppurating wounds, boils, anthrax, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as oneumonia, bronchitis and diphtheria. The products of the present invention are also active against infections caused by germs such as Haemophilus influenzae.

Therefore a subject of the invention is the compounds of formula (I) as medicaments.

A more particular subject of the invention is, as medicaments, the compounds indicated above as preferred compounds.

A subject of the invention is also the pharmaceutical compositions containing at least one of the medicaments defined above as active ingredient.

These compositions can be administered by buccal, rectal, parenteral route, or by local route as a topical application on the skin and mucous membranes, but the preferred administration route is the buccal or injectable route.

They can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example, a pyrogenic sterile water.

The dose administered is variable according to the affection treated, the patient in question, the administration route and the product considered. It can be, for example, comprised between 50 mg and 3000 mg per day by oral or injectable route for an adult for the preferred products.

A subject of the invention is also a process for the preparation of the compounds of formula (I), characterized in that a compound of formula (II):

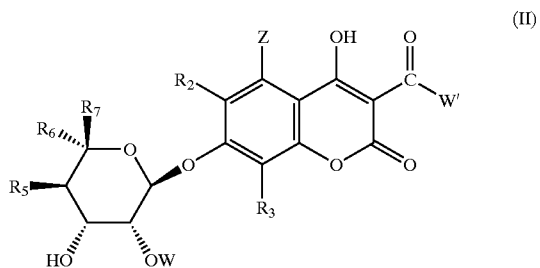

in which the radicals $R_2$, $R_3$, Z, $R_5$, $R_6$ and $R_7$ retain their previous meaning, OW represents a blocked hydroxyl group and W' represents an alkyl or Oalkyl radical containing up to 4 carbon atoms, is subjected to the action of an agent capable of introducing the

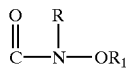

radical or of a series of operations capable of introducing the

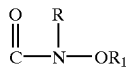

radical R and $R_1$ retaining their previous meaning, to the action of an agent capable of releasing the hydroxyl radical from the OW radical, to the optional action of an agent capable of replacing W' by the X radical which is different from alkyl or Oalkyl, to the optional action of an agent capable of introducing the Y radical which is different from oxygen, to the optional action of a salification agent.

The products of formula (II) used at the start of the process of the invention are new products, the preparation of certain products of formula (II) is given hereafter in the experimental part.

The other products of formula (II) can be synthesized by analogy with the processes described in the experimental part.

A more particular subject of the invention is the compounds of formula (II) the preparation of which is given in the experimental part.

In a preferred embodiment:.
The introduction of the

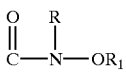

radical is carried out in several stages, firstly the action of a substituted or unsubstituted phenylchloroformate, then the action of a compound of formula $R_1ONHR$ in which $R_1$ and R retain their previous meaning
the OH group is blocked in the form of a tetrahydropyrane,
the release of the hydrolysis by acid hydrolysis, for example by the action of paratoluenesulphonic acid,
the optional conversion of the W' radical to the X radical and the conversion of the Y radical is carried out according to the standard processes. For the Y radical, it is in particular the action of an amine.

A subject of the invention is also a process characterized in that the product of formula (II) is prepared by the action of a compound of formula (III)

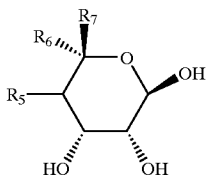

(III)

in which $R_5$, $R_6$ and $R_7$ retain their previous meaning on a compound of formula (IV)

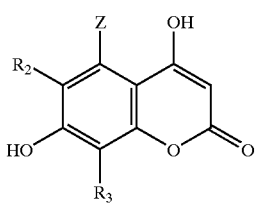

(IV)

in which $R_2$, $R_3$ and Z retain their previous meaning, then of a blocking agent of the free hydroxyl radical.

The following compounds of formula (III) are new and are in themselves a subject of the present invention, namely:

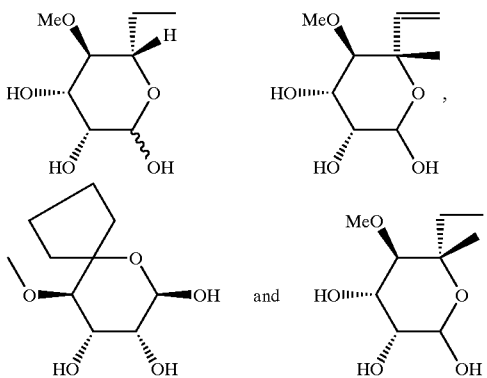

The following examples illustrate the invention without however limiting it.

Preparation 1: ethyl 7-[[6-deoxy-5-C-methyl-4-O-methyl-2-O-(tetrahydro-2H-pyrane-2-yl)-alpha-L-lyxo-hexopyranosyl]oxy]-4-hydroxy-8-methyl-2-oxo-2H-1-benzopyrane-3-carboxylate STAGE A: ethyl 7-[(6-deoxy-5-C-methyl-4-O-methyl-alpha-L-lyxo-hexopyranosyl)oxy]-8-methyl-2-oxo-4-(phenylmethoxy)-2H-1-benzopyrane-3-carboxylate A solution containing 80 g of ethyl 7-hydroxy-8-methyl-2-oxo-4-(phenylmethoxy)-2H-1-benzopyrane-3-carboxylate in 1200 ml of methylene chloride is agitated under an argon atmosphere. 52.07 g of 6-deoxy-5-C-methyl-4-O-methyl-L-lyxo-hexopyranose and 71.22 g of triphenylphosphine are added at 0° C.

54.78 ml of diisopropyl azocarboxylate is introduced at 0° C. After one hour of reaction at ambient temperature, 34 g of triphenylphosphine and 25.6 ml of diisopropyl azocarboxylate are added again. Agitation is carried out for 16 hours at ambient temperature followed by evaporation to one-half volume and filtering the suspension elutina with the toluene/isopropyl alcohol mixture (95-5). When the product starts to pass through, a mixture with 6% isopropyl alcohol is carried out. After saponification in 700 ml of hexane/ethyl acetate mixture (4-1), 64.4 g of sought product is obtained that is used as it is in the following stage.

STAGE B: ethyl 7-[(6-deoxy-5-C-methyl-4-O-methyl-3-O-(triethylsilyl)-alpha-L-lyxo-hexopyranosyl)oxy]-8-methyl-2-oxo-4-(phenylmethoxy)-2H-1-benzopyrane-3-carboxylate 50 g of a solution from stage A in 500 ml of methylene chloride is agitated under arcon at ambient temperature. 42 ml of diisopropylethylamine and 9.66 g of imidazole are added. The solution is agitated for 15 minutes or cooled down to 0° C., 20.64 ml of triethylchlorosilane is added dropwise over 30 minutes, and agitation is carried out for 2 hours at 0° C. The reaction medium is poured into a molar solution of sodium dihydrogen phosphate. Extraction is carried out with methylene chloride followed by drying and evaporating to dryness. 66.27 g of product is recovered that is purified on silica eluting with a methylene chloride mixture at 0.75% of acetone. When the product is nearly isolated,, eluting is carried out with a methylene chloride solution at 1% of acetone. 41.04 g of sought product is obtained after saponification in a hexane/ethyl acetate mixture (9-1).

NMR 1H (300 MHz, CDCl3, ppm) 0.73 (q, 6H), 1.04 (t, 9H), 1.04 (s, 3H);, 1.30 (s, 3H), 1.40 (t, 3H), 2.24 (s, 3H), 2.74 (d, J=1 Hz, mobile 1H), 3.28 (d, 1H, J=9), 3.53 (s, 3H), 4.05 (m, 1H), 4.27 (dd, 1H, J=3.5 and 9 Hz), 4.43 (q, 2H), 5.31 (s, 2H), 5.62 (d, 1H, J=2 Hz), 7.12 (d, 1H, J=9 Hz), 7.43 (m, 5H), 7.63 (d, 1H, J=9 Hz).

STAGE C: ethyl 7-[[6-deoxy-5-C-methyl-4-O-methyl-2-O-(tetrahydro-2H-pyrane-2-yl)-3-O-(triethylsilyl)-alpha-L-lyxo-hexopyranosyl]oxy]-8-methyl-2-oxo-4-(phenylmethoxy)-2H-1-benzopyrane-3-carboxylate A solution containing 40.9 g of product of the previous stage in 400 ml of methylene chloride is agitated under argon at ambient temperature. A few drops of paratoluene sulhonic acid, then 11.54 ml of dihydropyrane are added. Agitation is carried out for 2 hours at ambient temperature. 6 g of bisodium carbonate is added. The suspension is agitated for 15 minutes followed by diluting with 1000 ml of a hexane/ethyl acetate mixture (2-1) and pouring onto water. The reaction mixture is decanted, the organic phase is dried over sodium sulphate and evaporated to dryness. 54.67 g of product is obtained that is purified eluting with a hexane/ethyl acetate mixture (4-1). 36.83 g of product is thus obtained.

STAGE D: ethyl 7-[[6-deoxy-5-C-methyl-4-O-methyl-2-O-(tetrahydro-2H-pyrane-2-yl)-3-O-(triethylsilyl)-alpha-L-lyxo-hexopyranosyl]oxy]-4-hydroxy-8-methyl-2-oxo-2H-1-benzopyrane-3-carboxylate 18 g of product prepared in the previous stage are hydrogenated in solution in 360 ml of tetrahydrofurane in the presence of 0.240 g of palladium on carbon followed by filtering. The catalyst is washed with a little tetrahydrofurane. 100 ml of solvent is evaporated and a solution is obtained which is used as it is in the following stage.

STAGE E: ethyl 7-[[6-deoxy-5-C-methyl-4-O-methyl-2-O-(tetrahydro-2H-pyrane-2-yl)-alpha-L-lyxo-hexopyranosyl]oxy]-4-hydroxy-8-methyl-2-oxo-2H-1-benzopyrane-3-carboxylate A solution containing 15.31 g of product from the previous stage in 250 ml of tetrahydrofurane is cooled down under argon to 0° C. 31 ml of tetrabutylammonium fluoride (1M in THF) is added dropwise. The reaction medium is diluted with 400 ml of a hexane/ethyl acetate mixture (1-2). 300 ml of a solution of 10% of sodium hydrogen sulphate is added followed by decanting, drying and evaporating to dryness. The crude product obtained is solubilized in 20 ml of ethyl ether. The reaction medium is cooled down to −10° C. and 80 ml of pentane is added under agitation. The suspension obtained is acitated at −20° C., followed by filtering at −16° C. The product obtained is washed with the centane and dried. 9.4 g of sought product is obtained.

Preparation 2: 3-acetyl-7-[[6-deoxy-5-C-methyl-4-O-methyl-2-O-(tetrahydro-2H-pyrane-2-yl)-alpha-L-lyxo-hexopyranosyl]oxy]-4-hydroxy-8-methyl-2H-1-benzopyrane-2-one STAGE A: 4-(diphenylmethoxy)-8-methyl-7-(tetrahydro-2H-pyrane-2-yl)-2H-1-benzopyrane-2-one 55 g of 4-hydroxy-8-methyl-7-tetrahydro-2H-pyrane-2-yl)-2H-1-benzopyrane-2-one is added to 250 ml of anhydrous dimethylformamide heated to 40° C., and a solution of 58.3 g of diphenyldiazomethane in 250 ml of dimethyl formamide is added dropwise. The addition is carried out over 3 hours whilst maintaining the temperature at 40° C.

Several portions of 3 g of diphenyldiazomethane are added again and agitation is carried out for one hour at 40° C.

The reaction medium is poured onto 2 l of sulphuric ether. The organic solution is washed with an aqueous solution of sodium bicarbonate, with solution of soda (0.1 M), with water and salt water followed by evaporation to dryness. The residue is agitated in an isopropyl ether-hexane mixture (1-2). The insoluble part is separated and dried. 20.5 g of sought product is obtained.

CCM $CH_2Cl_2$-AcOEt (95-5). Rf=0.44.

STAGE B: 4-(diphenylmethoxy)-7-hydroxy-8-methyl-2H-1-benzopyrane-2-one 35 ml of a 0.9 M solution of hydrochloric acid in methanol are added to a solution containing a mixture of 20 g of the product of stage A, 100 ml of dichloromethane and 100 ml of methanol. Agitation is carried out for 2 hours at ambient temperature and the solvents are evaporated. The residue is taken up in absolute ethanol cooled down to 0° C. The insoluble part is separated and rinsed with ice cold alcohol then with sulphuric ether followed by drying. 15.53 g of product is recovered which is taken up in ether, separated and dried. 14.54 g of sought product is obtained.

NMR 1H (300 MHz, $CDCl_3$, ppm) 2.31 (s, 3H), 5.62 (s, 1H), 6.35 (s, 1H), 6.78 (d, 1H, J=_Hz), 7.75 (d, 1H, J=_Hz), 6.99 to 7.10 (m, _H), 7.30 to 7.42 (m, _H).

STAGE C: 7-[(6-deoxy-5-C-methyl-4-O-methyl-alpha-L-lyxo-hexopyranosyl)oxy]-4-(diphenylmethoxy)-8-methyl-2H-1-benzopyrane-2-one A mixture of 91.13 g of the product of stage B, 58.6 g of 6-deoxy-5-C-methyl-4-O-methyl-L-lyxo-hexopyranose and 80 g of triphenylphosphine in 900 ml of dichloromethane are cooled down to 0° C. 60 ml of diisopropylazodicarboxylate is added dropwise. Agitation is carried out for 1 hour at ambient temperature.

34 g of triphenylphosphine and 25 ml of diisopropylazodicarboxylate are added. Agitation is carried out for 1 hour at ambient temperature. 34 g of triphenylphosphine and 25 ml of diisopropylazodicarboxylate are added and agitation is carried out for 12 hours at ambient temperature. Concentration is carried out under reduced pressure. Chromatography is carried eluting with a toluene/isopropyl. alcohol mixture (95-5). After combining the fractions and evaporation of the solvents, 86.83 g of sought product is recovered after recrystallization from isopropyl ether.

NMR 1H (300 MHz, $CDCl_3$, ppm) 1.13 (s, 3H), 1.37 (s, 3H), 2.24 (s, 3H), 2.69 (s, 1H), 2.79 (s, 1H), 3.38 (d, 1H, J=10 Hz), 3.60 (s, 3H), 4.24 (m, 1H), 4.28 (m, 1H), 5.56 (s, 1H), 5.64 (d, 1H, J=1.5 Hz), 6.35 (s, 1H), 7.18 (d, 1H), 7.81 (d, 1H), 7.39 (m, 10 H).

STAGE D: 7-[[6-deoxy-5-C-methyl-4-O-methyl-3-O-(triethylsilyl)-alpha-L-lyxo-hexopyranosyl]oxy]-4-(diphenylmethoxy)-8-methyl-2H-1-benzopyrane-2-one 26.6 g of imidazole and 70.15 ml of diisopropylethylamine are added to a solution cooled down to 0° C., containing 80 g of the product of the previous stage and 600 ml of dichloromethane. 33.5 ml of triethylsilyl chloride is added dropwise. Agitation is carried out for 1 hour at ambient temperature followed by washing with an acueous solution of sodium dihydrogen phosphate (1M), with water and with salt water, drying over magnesium sulphate, filtering and concentration. 97.58 g of product is recovered which is purified by chromatography on silica eluting with the dichloromethane acetone mixture (0.8 to 1%). 46.5 g of product is obtained.

NMR 1H (300 MHz, $CDCl_3$-d6, ppm) 0.60 (q, _H, J=_Hz), 0.74 (q, _H, J=_Hz), 0.97 (t, _H, J=_Hz), 1.00 (t, _H, J=_Hz), 1.10 (s, 3H), 1.32 (s, 3H), 2.24 (s, 2H), 2.74 (s, 1H), 3.31 (d, 1H, J=_Hz), 3.54 (s, 3H), 4.07 (m, 1H), 4.29 (dd, 1H, J=_Hz), 5.50 (s, 1H), 5.64 (d, 1H, J=_Hz, 6.35 (s, 1H), 7.28 (d, 1H, J=_Hz), 7.81 (d, 1H, J=_Hz), 7.40 (m).

STAGE E: 7-([6-deoxy-5-C-methyl-4-O-methyl-2-O-(tetrahydro-2H-pyrane-2-yl)-3-O-(triethylsilyl)-alpha-L-lyxo-hexopyranosyl]oxy]-4-(diphenylmethoxy)-8-methyl-2H-1-benzopyrane-2-one 19 ml of dihydropyrane and 400 mg of paratoluene sulphonic acid (PTSA) are added to a solution containing 67 g of the product of the previous stage and 1 l of dichloromethane. Agitation is carried out for 40 minutes at ambient temperature, 300 mg of FTSA is added. After 30 minutes, 100 mg of PTSA is added, then another 100 mg of PTSA. Agitation is carried out for 20 more minutes, then finely ground sodium hydrogen carbonate is introduced. Agitation is carried out for 10 minutes, the reaction medium. is diluted with a hexane/ethyl acetate mixture (1-2), washed with water and with salt water followed by drying, filtering and evaporating the solvents. The product obtained is chromatographed eluting with a heptane/ethyl acetate mixture (4-1). 77.9 g of sought product is recovered.

NMR 1H (300 MHz, DMSO-$d_6$, ppm) 0.64 (q, _H, J=_Hz), 0.73 (q, _H, J=_Hz), 0.95 to 1.32 (_H), 2.25 (s, _H), 2.27 (s, _H), 3.30 (d, _H, J=_Hz), 3.4 (d, _H, J=_Hz), 3.50 (m, 2H), 3.93 (m, 2H), 3.53 (s, _H), 3.54 (s, _H), 4.04 to 4.15, 4.36 (dd, _H, J=_Hz), 4.94 (l), 4.96 (l), 5.50 (sl, _H), 5.65 (bs), 6.37 (s, 1H), 7.15 (d, _H, J=_Hz), 7.19 (d, _H, J=_Hz), 7.81 (m, 1H), 7.30 to 7.44, 1.47 to 2.00.

STAGE F: 7-[[6-deoxy-5-C-methyl-4-O-methyl-2-O-(tetrahydro-2H-pyrane-2-yl)-3-O-trimethylsilyl)-alpha-L-lyxo-hexopyranosyl]oxy]-4-hydroxy-8-methyl-2H-1-benzopyrane-2-one 15 g of the product of the previous stage is hydrogenated in 150 ml of absolute ethanol in the presence of palladium on carbon (2 g, 10%'). The catalyst is eliminated by filtration and the solvents are evaporated to dryness.

14.4 g of product is obtained.

STAGE G: 3-acetyl-7-[[6-deoxy-5-C-methyl-4-O-methyl-2-O-(tetrahydro-2H-pyrane-2-yl)-3-O-(triethylsilyl)-alpha-L-lyxo-hexopyranosyl]oxy]-4-hydroxy-8-methyl-2H-1-benzopyrane-2-one 6.52 g of dimethylaminopyridine are added to a solution containing 14.37 g of the product of the previous stage and 150 ml of dichloromethane. 2.72 ml of acetic anhydride is introduced dropwise. Agitation is carried out at ambient temperature under argon for 1 hour followed by diluting with 200 ml of dichloromethane, washing with an aqueous solution of sodium dihydrogen phosphate, drying over magnesium sulphate, filtering and concentrating. 14.9 g of sought product is obtained.

STAGE H: 3-acetyl-7-[[6-deoxy-5-C-methyl-4-O-methyl-2-O-(tetrahydro-2H-pyrane-2-yl)-alpha-L-lyxo-hexopyranosyl]oxy]-4-hydroxy-8-methyl-2H-1-benzopyrane-2-one 27 ml of a 1M solution of tetrabutylammonium fluoride in tetrahydrofurane is introduced dropwise at 0° C. to a solution containing 15.2 ml of the product of the previous stage in 250 ml of THF. Agitation is carried out under arcon for 48 hours at ambient temperature. The medium is diluted with an ethyl acetate/hexane mixture, washed with water and with salt water followed by dryinga filtering and concentrating to dryness 13 g of a product is obtained which is triturated in pentane, the supernatant is eliminated and the operation is repeated several times. The product is maintained at +4° C., ground in the presence of pentane, the insoluble part is filtered, rinsed and dried. 6.99 g of sought product is obtained.

NMR 1H (300 MHz, $CDCl_3$-d6, ppm) 1.09 (s, 3H), 1.11 (s, 3H), 1.35 (s, 3H), 1.36 (s, 1H), 1.50 to 1.90 (m, 8), 2.23 (s, 3H), 2.24 (s, 3H), 2.76 (s, 3H), 3.28 (d, 1H, J=_Hz), 3.33 (d, 1H, J=_Hz), 3.63 (s, 3H), 3.64 (s, 3H), 3.54 (m), 3.97 (m), 4.07 (m), 4.20 to 4.30 (_, 2H), 4.59 (m, _H), 4.82 (m, _H), 5.63 (bs, _H), 5.85 (bs, _H), 7.20 (d, 1H, J=_Hz), 7.88 (m, _H).

EXAMPLE 1

(2-propynyloxy)-carbamic 3'ester of 7-[[6-deoxy-5-C-methyl-4-O-methyl-alpha-L-lyxo-hexopyranosyl]oxy]-4-hydroxy-8-methyl-2-oxo-2H-1-benzopyran-3-carboxamide acid

STAGE A: 3-(4-nitrophenylcarbonate) of ethyl 7-[[6-deoxy-5-C-methyl-4-O-methyl-2-O-(tetrahydro-2H-pyrane-2-yl)-alpha-L-lyxo-hexopyranosyl]oxy]-4-hydroxy-8-methyl-2-oxo-2H-1-benzopyrane-3-carboxylate 4 g of the product of preparation 1 is dissolved under argon in 80 ml of methylene chloride. 2.15 g of dimethylaminopyridine and at 0° C., 2 g of 4-nitrophenylchloroformate are added. Agitation is carried out for 1 hour at 0° C. The methylene chloride is evaporated and the sought product is obtained.

STAGE B: ethyl 7-[[6-deoxy-5-C-methyl-4-O-methyl-3-O-[[(2-propynyloxy)amino]carbonyl]-2-O-(tetrahydro-2H-pyrane-2-yl)alpha-L-lyxo-hexopyranosyl]oxy]-4-hydroxy-8-methyl-2-oxo-2H-1-benzopyrane-3-carboxylate 1.215 g of O-propargylhydroxylamine chlorohydrate is dissolved in 40 ml of dimethylformamide. At 0° C., 0.392 g of sodium hydride (in 50% of oil) is added and agitation is carried out for an hour at this temperature. 4 ml of solution of the product prepared in the previous stage in dimethylformamide and 940 mg of dimethylaminopyridine are introduced at 0° C. into this suspension. Agitation is carried out for 1 hour at 0° C. followed by diluting with a hexane/ethyl acetate mixture (1-2). The organic solution is washed with 400 ml of sodium hydrogen sulphate solution at 10%, dried over sodium sulphate and evaporated to dryness. 7.87 g of crude sought product is obtained.

STAGE C: 7-[[6-deoxy-5-C-methyl-4-O-methyl-2-O-(tetrahydro-2H-pyrane-2-yl)alpha-L-lyxo-hexopyranosyl]oxy]-4-hydroxy-8-methyl-2-oxo-2H-1-benzopyrane-3-carboxamide (2-propynyloxy)-carbamic 3'-ester acid 2 g of the product of the previous stage is dissolved in 50 ml of tetrahydrofurane. The solution obtained is saturated with ammonium hydroxide at 0° C. for 10 minutes and agitated for 48 hours at ambient temperature followed by diluting with 100 ml of a hexane/ethyl acetate mixture (1-1). The organic solution is washed with 100 ml of a 1M sodium dihydrogen phosphate solution, then it is dried over magnesium sulphate and evaporated to dryness. 2 g of the sought product is obtained.

STAGE D: 7-[[6-deoxy-5-C-methyl-4-O-methyl-alpha-L-lyxo-hexopyranosyl]oxy]-4-hydroxy-8-methyl-2-oxo-2H-1-benzopyrane-3-carboxamide (2-propynyloxy)-carbamic 3'ester acid 2 g of the product of the previous stage and 200 mg of p-toluene-sulphbnic acid are dissolved in 20 ml of methanol. Agitation is carried out for 1 hour followed by diluting with 100 ml of hexane/ethyl acetate mixture (1-1), washing with a saturated solution of sodium dihydrogen phosphate, drying and bringing to dryness. 1.6 g of product is obtained which is purified eluting with an 8% methylene chloride/methanol mixture followed by impasting with an ethyl ether/pentane mixture. 0.574 g of sought product is obtained.

NMR 1H (300 MHz, DMSO-d6, ppm) 1.04 (s, 3H), 1.26 (s, 3H), 2.20 (s, 3H), 3.45, (s, 3H), 3.52 (d, 1H), 3.56 (m, 1H), 4.14 (m, 1H), 4.46 (m, 2H), 5.20 (m, 1H), 5.59 (bs, 1H), 5.77 (d, mobile 1H), 7.22 (d, 1 Hz), 7.83 (d, 1H), 8.71 (m) and 8.96 (m). (mobile 2H's).

EXAMPLE 2

7-[(6-deoxy-5-C-methyl-4-O-methyl-alpha-L-lyxo-hexopyranosyl)oxy]-4-hydroxy-8-methyl-N-[2-(4-morpholinyl)ethyl]-2-oxo-2H-1-benzopyrane-3-carboxamide (2-propynyloxy)-carbamic 3'-ester acid STAGE A: 7-[[6-deoxy-5-C-methyl-4-O-methyl-2-O-(tetrahydro-2H-pyrane-2-yl)-alpha-L-lyxo-hexopyranosyl]oxy]-4-hydroxy-8-methyl-N-[2-(4-morpholinyl)ethyl]-2-oxo-2H-1-benzopyrane-3-carboxamide (2-propynyloxy)carbamic 3'-ester acid 7.5 ml of 2-(4-morpholino)ethylamine is introduced into a solution containing 1 g of the product of stage B of Example 1 in 4 ml of tetrahydrofurane. Agitation is carried out for 24 hours at ambient temperature followed by diluting with 100 ml of hexane/ethyl acetate/tetrahydrofurane (1-4-1), washing with a saturated solution of sodium dihydrogen phosphate, drying over magnesium sulphate and evaporating to dryness. 1 g of sought product is obtained.

STAGE B: 7-[(6-deoxy-5-C-methyl-4-O-methyl-alpha-L-lyxo-hexopyranosyl)oxy]-4-hydroxy-8-methyl-N-[2-(4-morpholinyl)ethyl]-2-oxo-2H-1-benzopyrane-3-carboxamide (2-propynyloxy)-carbamic 3'-ester acid 0.97 mmoles of the product of the previous stage is dissolved in 10 ml of-methanol. 100 mg of p-toluenesulphonic acid is added. Agitation is carried out for 1 hour at ambient temperature. A further 80 mg of p-toluenesulphonic acid is added. Agitation is carried out for 3 hours followed by diluting with 50 ml of a hexane/ethyl acetate mixture (1-3), washing with 75 ml of a 1M solution of sodium dihydrogen phosphate, drying over magnesium sulphate and evaporating to dryness. The product is purified by chromatography on silica eluting with a methylene chloride/methanol mixture (91-9). The product obtained is impasted in an ethyl ether/pentane mixture. 0.150 g of sought product is obtained.

NMR 1H (300 MHz, DMSO-d6, ppm) 1.03 (s, 3H), 1.27 (s, 3H), 2.21 (s, 3H), 2.50 (masked, 4H), 2.57 (t, 2H), 3.45 (s, 3H), of 3.40 to 3.69 (m, 4H), 4.13 (m, 1H), 4.47 (d, 2H, J=2.5 Hz), 5.20 (dd, 1H, J=3 and 10 Hz), 5.60 (d, 1H, J=2 Hz), 5.77 (d, 1H, J=5 Hz), 7.21 (d, 1H, J=9 Hz), 7.84 (d, 1H, J=9 Hz), 9.45 (t, mobile 1H) 10.72 (m, mobile 1H).

EXAMPLE 3

7-[[6-deoxy-5-C-methyl-4-O-methyl-alpha-L-lyxo-hexopyranosyl]oxy]-4-hydroxy-3-[1-(methoxyimino)ethyl]-8-methyl-2H-1-benzopyran-2-one(2-propynyloxy)-carbamic-3'-ester acid STAGE A: 7-[6-deoxy-5-C-methyl-4-O-methyl-2-O-(tetrahydro-2H-pyran-2-yl)-alpha-L-lyxo-hexopyranosyl]oxy]-4-hydroxy-3-(1-(methoxyirmino)ethyl-8-methyl-2H-1-benzopyran-2-one A solution containing 1.2 g of the product of Preparation 2 is heated at 40° C. in the presence of 0.597 g of potassium acetate and 0.407 mg of O-methylhydroxylamine hydrochloride. The reaction medium is agitated for one hour and 30 minutes at 40° C., followed by diluting with an ethyl acetate/hexane mixture (4-1), washing with 150 ml of a solution of sodium hydrogen phosphate, rinsing with water, drying, filtering and evaporating to dryness.

STAGE B: 7-[[6-deoxy-5-C-methyl-4-O-methyl-2-O-(tetrahydro-2H-pyran-2-yl)-alpha-L-lyxo-hexopyranosyl]oxy]-4-hydroxy-3-[1-(methoxyimino)ethyl]-8-methyl-2H-benzopyran-2-one3-(4-nitrophenylcarbonate)

0.390 g of dimethylaminopyridine is added to a solution containing 1.28 mmoles of the product of the previous stage and 12 ml of dichloromethane. 0.319 g of 4-nitrophenyl chloroformate is added. Agitation is carried out for 30 minutes at 0° C. The methylene chloride is evaporated and the product obtained is dried. 1.218 nmoles of sought product are thus obtained.

STAGE C: 7-[[6-deoxy-5-C-methyl-4-O-methyl-2-O-(tetrahydro-2H-pyran-2-yl)alpha-L-lyxo-hexopyranosyl]oxy]-4-hydroxy-3-[1-(methoxyimino)ethyl]-8-methyl-2H-1-benzopyran-2-one(2-propynyloxy)-carbamic 3'-ester acid 0.240 g of sodium hydride (with 55% of mineral oil) is added to a solution cooled down to 0° C. of 0.655 g of O-propargylhydroxylamine hydrochloride in 6 ml of dimethylformamide. Agitation is carried out for 30 minutes at 0° C. and the reaction medium is poured into a solution containing 1.218 mmoles of the product of the previous stage and 6 ml of DMF in the presence of 0.150 g of dimethylaminopyridine. After one hour at 0° C., the reaction mixture is poured into an ethyl acetate/hexane mixture at 20%, washed with a solution of sodium hydrogen sulphate at 10%, with water and with salt water. The solvents are dried and evaporated to dryness. 0.865 g of sought product is obtained.

STAGE D: 7-[(6-deoxy-5-C-methyl-4-O-methyl-alpha-L-lyxo-hexopyranosyl]oxy]-4-hydroxy-3-[1-(methoxyimino)ethyl]-8-methyl-2H-1-benzopyran-2-one(2-propynyloxy)-carbamic-3'-ester acid 150 mg of PTSA is added to a solution containing 1.218 mmoles of the product of the previous stage and 12 ml of methanol. Agitation is carried out for one hour at ambient temperature followed by diluting with an ethyl acetate/hexane (1-1) mixture and washing with an aqueous solution of sodium dihydrogen phosphate 1M, then with salt water. The organic phase is dried over magnesium sulphate. The solvents are evaporated to dryness. The product obtained is chromatographed eluting with a dichloromethane/acetone (85-15) mixture, and 0.394 g of product is obtained which is dissolved again in ether and precipitated with pentane. The insoluble part is isolated by filtration and dried under reduced pressure. 0.380 g of sought product is thus obtained.

EXAMPLE 4

7-[(6-deoxy-5-C-methyl-4-O-methyl-alpha-L-lyxo-hexopyranosyl)oxy]-3-[1-(ethoxyimino)ethyl]-4-hydroxy-8-methyl-2H-1-benzopyran-2-one(2-propynyloxy)-carbamic 3'-ester acid Operating as previously, the sought product was obtainer. NMR CDCl$_3$, ppm 1.17 (s) - 1.38 (s): 2 CH3 Gem; 1.38 (t): CH3CH2O; 1.61 (s): 4 mobile, 2.25 (s) - 2.53 (s): 2CH3—C(=O)—; 2.57

(t): J=2.5 h-C C—; 2.64 (bs) OH—CH; 3.54 (s): OCH3; 3.61 (d): J=9.5 H4 rex; 4.23 (q) slightly deficient CH3—CH2—O; 4.43 (bs): H2 eq; 4.57 (d): 2H OCH2—C CH; 5.46 (dd): J=2.5 and 9.5 H3 ox; 5.61 (d): J=2.5 H1 eq; 7.12 (d): H'6; 7.77 (d): H'5; mobile H's 7.78: 14.15 and 15.11

Absorptions along the spectrum 2.05 (acetone), 4.13, 4.75–4.60–15.67.

EXAMPLE 5

8-hydroxy-7-[4-hydroxy-3-[1-(methoxyimino)ethyl]-8-methyl-2-oxo-2H-1-benzopyran-7-yl]-10-methoxy-6-oxaspiro[4.5]decan-9-yl[7R-(7.alpha.,8.beta.,9.beta.,10.alpha.)]-(2propynyloxy)-carbamate The preparation of this product and that of the starting products used can be shown as follows:

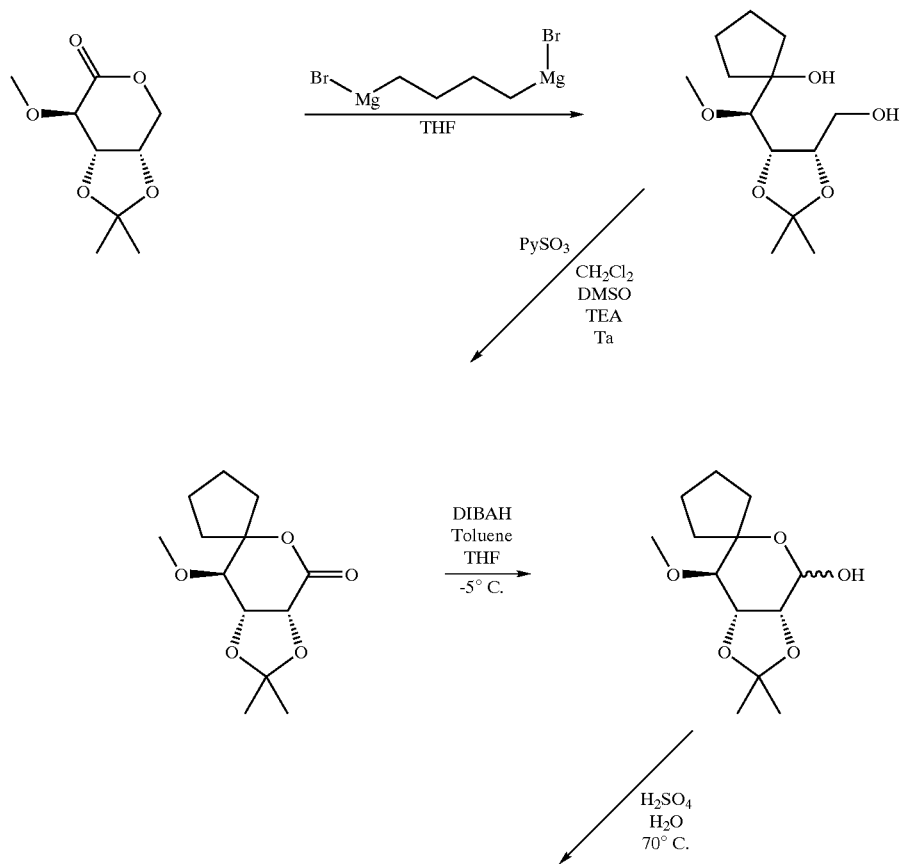

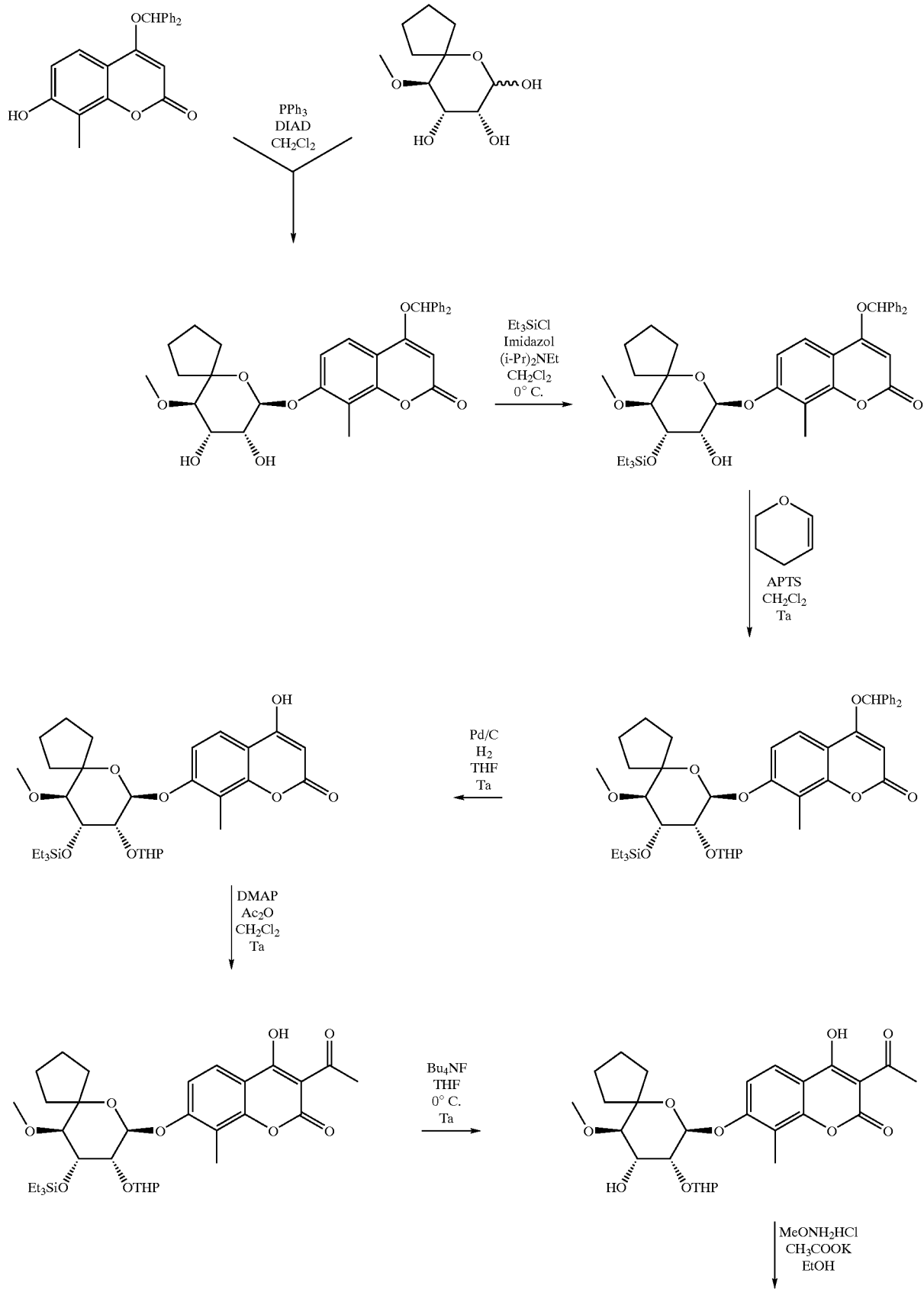

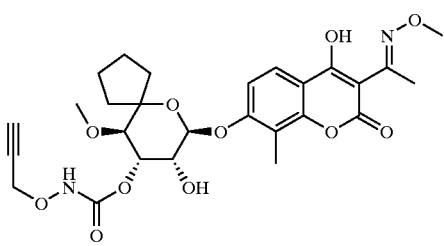

1) pNO₂C₆H₄OCOCl
DMAP
CH₂Cl₂

2) ≡—O—NH₂ HCl
NAH
DMAP
DMF

3) APTS
MeOH

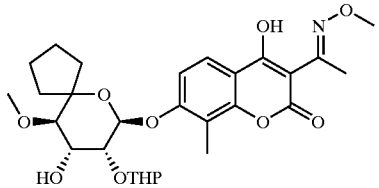

Preparation 3: [8R-(8.alpha.,9.alpha,10.beta)]-10-methoxy-6-oxaspiro[4.5]decan-7,8,9-triol

STAGE A: [4S-[4.alpha.,5.alpha.(S*)]]-2,2-dimethyl-5-[(1-hydroxycyclopentyl)methoxymethyl]-1,3-dioxolane-4-methanol 20 ml of a solution of dibromobutane (106 ml of dibromobutane in 200 ml of THF) is introduced into a mixture containing 43 g of magnesium, 100 ml of THF and one iodine crystal. The reaction mixture is subjected to ultrasound. 1.7 l of THF is added. The remainder of the dibrominated solution is added. Agitation is maintained for 2 hours 30 minutes. A solution containing 80.37 g of delta-lactone of 2-0-methyl-3,4-O-(1-methylethylidene)-L-arabinonic acid and 1 liter of THF is added at 17° C. Agitation is carried out for approximately 5 hours at ambient temperature. The reaction mixture is cooled down to 0° C., a solution saturated in ammonium chloride is added followed by decanting, drawing off the organic phase and extracting with a solution of ethyl acetate with 20% heptane. The reaction mixture is washed, dried and evaporated to dryness. 111.85 g of sought product is thus obtained.

STAGE B: [3'aS-(3'a.alpha.,7'.alpha,7'a.beta.)]-7'-methoxy-dihydro-spiro[cyclopentane-1.6'-[6H]-1,3-dioxolo[4,5-c]pyran]-4'(3aH)-one 221 g of pyridine sulphurtrioxide (PySO3) is added to a solution containing 111 g of the product prepared in Stage A and a mixture of a liter of methylene chloride, 1 liter of DMSO, 0.607 l of triethylamine. Agitation is carried out for 2 hours at ambient temperature. The reaction mixture is poured into an aqueous solution of phosphate acid phosphate, extracted with an ethyl acetate, heptane (1-1) mixture followed by drying, filtering and evaporating to dryness. 57.7 g of sought product is obtained.

STAGE C: [8R-(8.alpha.,9.alpha,10.beta)]-10-methoxy-6-oxaspiro[4.5]decane-7.8,9-triol 157 ml of a 1.5 M solution of dibutylaluminium hydride in toluene is added at −5° C. to a solution containing 56 g of the product of the previous stage and 300 ml of THF. Agitation is carried out at −3° C. for 1 hour. 1 liter of a 1 M solution of sodium potassium tartrate is added. Agitation is carried out for 15 minutes at ambient temperature. The reaction medium is extracted with an ethyl acetate-heptane 1-1 mixture followed by washing with water, salt water, drying and evaporating to dryness. The residue obtained is agitated at 70° C. in the presence of 150 ml of a solution of sulphuric acid 0.1 N and 150 ml of water for 2.5 hours. The reaction medium is cooled down to ambient temperature, barium carbonate is added, and agitation is carried out for 1 hour at ambient temperature followed by filtering and evaporating to dryness. 49 g of the sought product is obtained.

EXAMPLE 5

8-hydroxy-7-[4-hydroxy-3-[1-methoxyimino)ethyl]-8-methyl-2-oxo-2H-1-benzopyran-7-yl]-10-methoxy-6-oxaspiro[4.5]decan-9-yl[7R-(7.alpha.,8.beta.,9.beta.,10.alpha.)]-(2-propynyloxy)-carbamate

STAGE A: [7R-(7.alpha.,8.beta.,9.beta.,10.alpha.)]-7-[(8,9-dihydroxy-10-methoxy-6-oxaspiro[4.5]decan-7-yl)oxy]-4-(diphenylmethoxy)-8-methyl-2H-1-benzopyran-2-one 45.30 g of diisopropylazodicarboxylate (DIAD) is added dropwise at 0° C. to a mixture of 40 g of the product of preparation 3, 73 g of the product of stage B of preparation 2, namely 4-(diphenylmethoxy)-7-hydroxy-8-methyl-2H-1-benzopyran-2-one and 59 g of triphenylphosphine. Agitation is carried out for 1.5 hours at ambient temperature. 1 equivalent of triphenylphosphine and DIAD is added at 0° C. The solvents are evaporated, taken up in ether and the sought product obtained.

STAGE B: [7R-(7.alpha.,8.beta.,9.beta.,10.alpha.)]-4-(diphenylmethoxy)-7-[[8-hydroxy-10-methoxy-9-[(triethylsilyl)oxy]-6-oxaspiro[4.5]decan-7-yl)oxy]-8-methyl-2H-1-benzopyran-2-one 15.21 g of imidazole, 40.1 ml of diisopropylamine and 18.75 g of triethylsilane chloride are added at 0° C. to a solution containing 48 g of the product of the previous stage and 400 ml of methylene chloride. Agitation is carried out for 1 hour at 0° C., followed by washing with a 1 M solution of sodium acid phosphate and rinsing with water and drying. The product obtained is chromatographed on silica eluting with a methylene chloride/acetone 99-1 mixture then with a toluene/tertbutylmethyether mixture. 28.37 g of the sought product is obtained.

STAGE C: [7R-(7.alpha.,8.beta.,9.beta.,10.alpha.)]-4-(diphenylmethoxy)-7-[[10-methoxy-8-[(tetrahydro-2H-pyran-2-yl)oxy]-9-[(triethylsilyl)oxy]-6-oxaspiro[4.5]decan-7-yl)oxy]-8-methyl-2H-1-benzopyran-2-one 7.57 ml of 3,4-dihydropyran and 400 mg of paratoluene sulphonic acid are added to a solution containing 28.1 g of the product of the previous stage and 250 ml of dichloromethane. Agitation is carried out for 1 hour at ambient temperature. Bicarbonate of soda is added and agitated for 20 minutes at ambient temperature followed by washing with water, drying the organic phases on sodium sulphate. The product obtained is chromatographed on silica elutina with a heptane-ethyl acetate 4,1 mixture. 16.81 g of sought product is obtained.

STAGE D: [7R-(7.alpha.,8.beta.,9.beta.,10.alpha.)]-4-hydroxy-7-[[10-methoxy-8-[(tetrahydro-2H-pyran-2-yl)oxy]-9-[(triethylsilyl)oxy]-6-oxaspiro[4.5]decan-7-yl)oxy]-8-methyl-2H-1-benzopyran-2-one A solution of 16.19 g of the product of the previous stage, 150 ml of THF, is agitated under a hydrogen atmosphere in the presence of 810 mg of palladium on carbon followed by filtration, and 15.1 g of sought product is obtained.

STAGE E: [7R-(7.alpha.,8.beta.,9.beta.,10.alpha.)]-3-acetyl-4-hydroxy-7-[[10-methoxy-8-[(tetrahydro-2H-pyran-2-yl)oxy]-9-[(triethylsilyl)oxy]-6-oxaspiro[4.5]decan-7-yl)oxy]-8-methyl-2H-1-benzopyran-2-one 2.28 ml of acetic anhydride is added to a mixture containing 13.8 g of the product of the previous stage and 150 ml of methylene chloride and 5.94 g of dimethylaminopyridine (DMAP). Agitation is carried out for one hour at ambient temperature. The reaction medium is treated with a molar solution of sodium acid phosphate, extracted with methylene chloride, washed with water and dried. 16.21 g of sought product is obtained which is used as it is in the following stage.

STAGE F: [7R-(7.alpha.8.beta.,9.beta.,10.alpha.)]-3-acetyl-4-hydroxy-7-[[9-hydroxy-10-methoxy-8-[(tetrahydro-2H-pyran-2-yl)oxy]-6-oxaspiro[4.5]decan-7-yl)oxy]-8-methyl-2H-1-benzopyran-2-one 1.5 equivalent of a 1M solution of tetrabutylammonium fluoride in THF is added at 0° C. to a solution containing the product of the previous stage and 200 ml of THF. The reaction mixture is kept under agitation at ambient temperature for 15 hours. The reaction mixture is poured onto the heptane-ethyl acetate 30–70 mixture followed by washing with water, filtering and drying. A product is obtained which is used as it is in the following stage.

STAGE G: [7R-(7.alpha.,8.beta.,9.beta.,10.alpha.)]-4-hydroxy-7-[(9-hydroxy-10-methoxy-8-[(tetrahydro-2H-pyran-2-yl)oxy]-6-oxaspiro[4.5]decan-7-yl)oxy]-3-[1-(methoxyimino)ethyl]-8-methyl-2H-1-benzopyran-2-one 4.6 g of potassium acetate and 3.12 g of O-methylhydroxylamine hydrochloride are added to a solution containing 18.69 mmoles of the product of the previous stage and 100 ml of ethanol. Agitation is carried out for 1.5 hours at ambient temperature. The reaction medium is poured onto a 1M solution of sodium acid phosphate, extracted with a heptane/ethyl acetate 30-70 mixture followed by washing with water, drying and evaporating to dryness. The product obtained is chromatographed with a heptane-ethyl acetate (1:1) mixture. 6.54 g of sought product is obtained.

STAGE H: 8-hydroxy-7-(4-hydroxy 3-(1-(methoxyimino)ethyl]-8-methyl-2-oxo-2H-1-benzopyran-7-yl]-10-methoxy-6-oxaspiro[4.5]decan-9-yl[7R.(7.alpha.,8.beta.,9.beta.,10.alpha.)]-(2-propynyloxy)-carbamate 1) 3.70 g of DMAP and 3.05 g of para-nitrobenzene chloroformiate is introduced at 0° C. into a solution.

containing 6.37 g of the product of the previous stage and 70 ml of dichloromethane. Agitation is carried out for 1 hour at 0° C.

2) 2.3 g of sodium hydride is added at 0° C. to a solution containing 6.26 g of propargylhydroxylamine hydrochloride and 50 ml of DMF. Agitation is carried out for 1 hour at 0° C. The solution (1) is concentrated to dryness. The residue obtained is dissolved in 50 ml of DMF. 1.42 g of DMAP is added. The solution (2) is added at 0° C. to the solution thus obtained. Agitation is carried out for 1 hour at 0° C. The reaction medium is treated with sodium acid phosphate, washed with water, dried and concentrated to dryness. The residue obtained is dissolved in 100 ml of methanol. 2.1 g of PTSA is added and agitation is carried out at ambient temperature. The product obtained is chromatographed eluting with toluene and then with a toluene-isopropyl ether 92-8 mixture. The product is dispersed under ultrasound in an isopropyl ether-pentane mixture. The sought product is obtained.

NMR spectrum: CDCl$_3$ ppm

| | |
|---|---|
| 1.30 to 2.00 | CH$_2$ cycle |
| 2.20 (s) | C$_6$H$_5$—Me |
| 2.50 (s) | N=C—Me |
| 2.56 (t) | C—CH$_2$—C≡CH |
| 4.57 (d) | ... ↑ |
| 3.55 (s) | C—CMe |
| 3.65 (d, J=8) | H$_4$ax |
| 4.00 (s) | =N—OMe |
| 4.38 (sl) | H$_2$eq |
| 5.37 (dd) | H$_3$ax |
| 5.51 (d) | H1eq |
| 7.00 (d) | H6' |
| 7.66 (d) | H5' |
| 8.19 (bs) | NH |

Preparation 4

STAGE A:

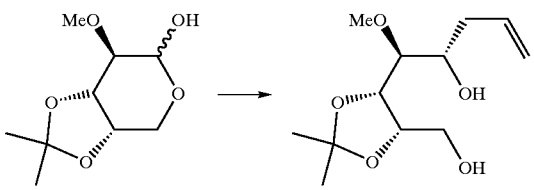

20.4 g of 2-0-methyl-3,4-0-(1-methylethyledene)L-arabinose is dissolved under an argon atmosphere in 200 ml of tetrahydrofurane. 200 ml of a 2 M solution of allylmagnesium bromide in tetrahydrofurane is added at 0° C. under argon. The solution is agitated for 1 hour at 0° C. The reaction medium is cooled down to −15° C. and is diluted with 100 ml of heptane. In order to neutralize the excess magnesium, 300 ml of an aqueous solution of sodium hydrogen sulphate at 10% is added dropwise. The organic phase is separated and the aqueous phase is extracted with a mixture of heptane 1/ethyl acetate 2. The organic phases are combined, dried over magnesium sulphate and evaporated to dryness. 22.96 g of sought product is obtained.

Yield: 94%

STAGE B:

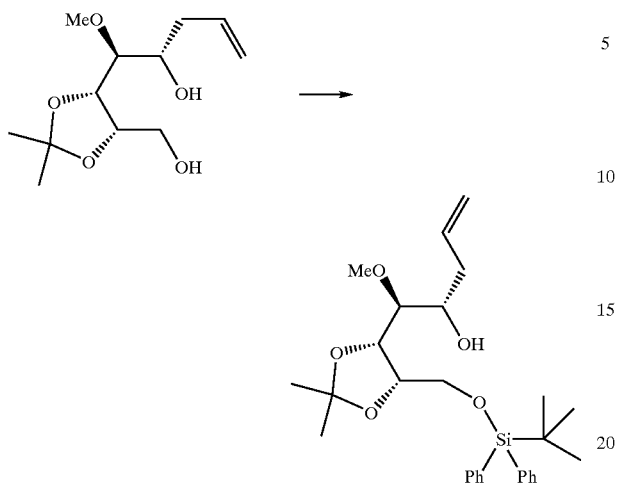

22.96 g of the product of the previous stage is dissolved under an argon atmosphere in 175 ml of dimethylformamide. 14.88 g of imidazole is added, then 23.31 ml of diphenylterbutylsilyl chloride is added dropwise at 0° C. under argon. The solution is agitated for 30 minutes at 0° C. The reaction medium is diluted with 400 ml of a heptane 1/ethyl acetate 2 mixture. The organic phase is washed twice with 200 ml of a 1 molar aqueous solution of sodium dihydrogen phosphate, dried over magnesium sulphate and evaporated to dryness. 45 g of resin product is obtained which is purified by chromatography on silica eluting with a heptane 4/ethyl acetate 1 mixture. 39.5 g of sought product is obtained.
Yield: 85%

STAGE C:

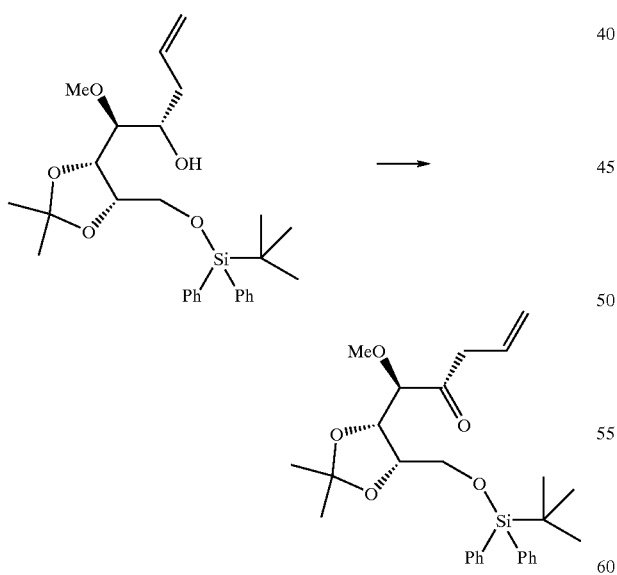

25.1 g of pyridinium chlorochromate is suspended in 200 ml of methylene chloride. 53.8 g of 4 Å molecular sieve is then added. 39.5 g of the product of the previous stage in solution in 100 ml of methylene chloride is then introduced into this suspension in one go. Agitation is carried out for 3 hours. The suspension is filtered followed by eluting with a methylene chloride 3% methanol mixture. The filtrate is evaporated to dryness. The residue obtained (35 g) is filtered on silica elutina with the heptane 4/ethyl acetate 1 mixture. 32.9 g of sought product is obtained.
Yield: 87%

STAGE D:

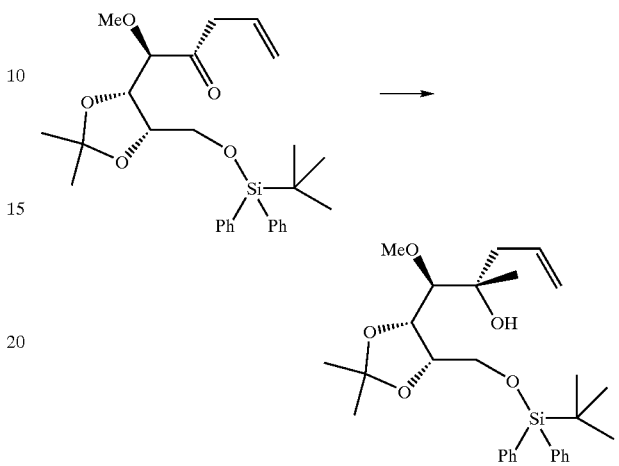

32.5 g of the product of the previous stage is dissolved in 250 ml of tetrahydrofurane. 60 ml of a methylmagnesium bromide solution in ether (3M) is added dropwise under argon at −5° C. Agitation is carried out for 1 hour at ambient temperature. The excess magnesium is neutralized at 0° C. with an aqueous solution of sodium hydrogen sulphate at 10%. 200 ml of a heptane 1/ethyl acetate 2 mixture is added. The organic phase is washed with 200 ml of an aqueous solution of sodium dihydrogen phosphate (M), dried over magnesium sulphate and evaporated to dryness. The product obtained is impasted in 200 ml of pentane/ether. 16.9 g of sought product is obtained.
Yield: 64%

STAGE E:

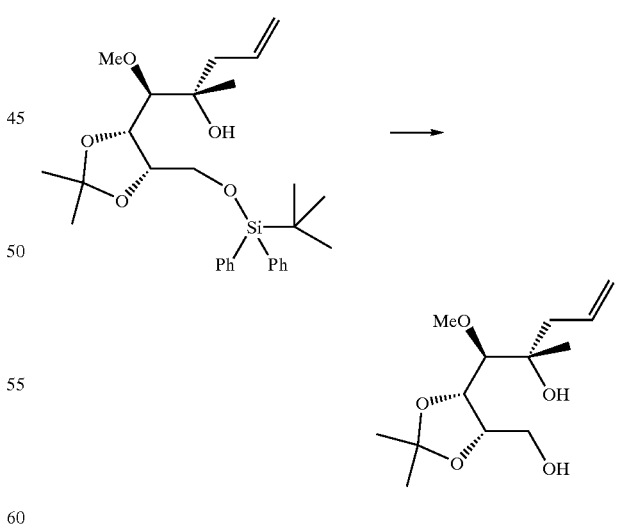

16.9 g of the product of the previous stage is dissolved in 150 ml of tetrahydrofurane. 68 ml of a molar solution of tetrabutylammonium fluoride in tetrahydrofurane is added dropwise under argon at 0° C. Agitation is carried out for 30 minutes at ambient temperature. 200 ml of a heptane 1/ethyl acetate 2 mixture is added. The organic phase is washed with 200 ml of a molar aqueous solution of sodium dihydrogen phosphate, dried over magnesium sulphate and evaporated to dryness. The crude product is purified by chromatography on silica eluting with a methylene chloride 95/methanol 5 mixture. 10.1 g of sought product is obtained.

STAGE F:

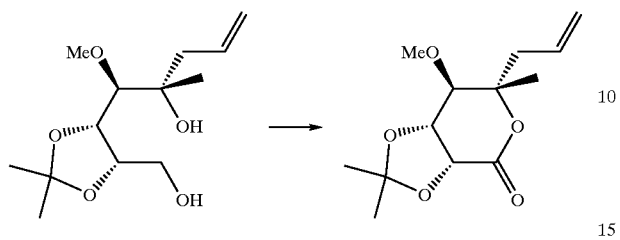

10.15 g of the product of the previous stage is dissolved in 103 ml of methylene chloride. 55 ml of triethylamine and 103 ml of dimethylsulphoxide stored on molecular sieve are added under aroon at ambient temperature. The solution is cooled down to approximately 5° C. with an ice-water bath and 19.77 g of pyridine sulphurtrioxide is added in fractions without the temperature exceeding 15° C. Aaitation is carried out for 1 hour. The reaction medium is poured into 1 liter of a molar aqueous solution of sodium dihydrogen phosphate, the aqueous phase is extracted twice with a heptane 1/ethyl acetate 2 mixture. The organic phase is washed with water, dried over magnesium sulphate and evaporated to dryness. The crude product crystallizes and is impasted in pentane. 6.8 g of sought product is obtained.
Yield: 68%

STAGE G:

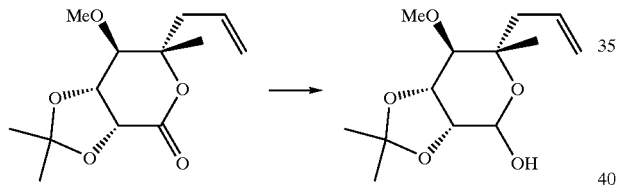

5.3 g of the product of the previous stage is dissolved in 30 ml of tetrahydrofurane. 13.85 ml of DIBAL is added under argon at −6° C. After 1 hour 30 minutes of agitation at 0° C., the reaction is terminated. The reaction medium is poured into 100 ml of a 1M solution of sodium potassium tartrate; the aqueous phase is extracted with a heptane 1/ethyl acetate 2 mixture. The organic phase is washed with 150 ml of an aqueous solution of sodium hydrogen sulphate at 10%, dried over magnesium sulphate and evaporated to dryness.
5.5 g of sought product is obtained.
Yield: Quantitative

STAGE H:

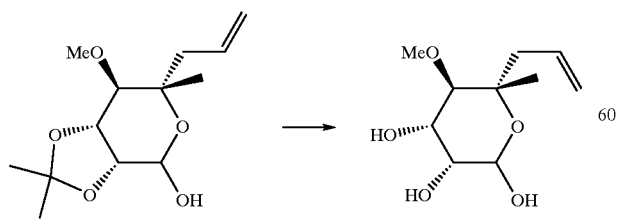

5.5 g of the product of the previous stage is emulsified in 32 ml of a solution of sulphuric acid at 0.05 N. After 1 hour 30 minutes of heating at 70° C., the reaction is terminated. The reaction medium is left to return to ambient temperature and is neutralized with 0.6 g of barium carbonate. The suspension is agitated for one hour at ambient temperature (pH=7), then filtered and evaporated to dryness. To dry the product, two distillations with toluene are carried out followed by drying and 4.4 g of sought product is obtained.
Yield: 96%

EXAMPLE 6

7-[[6-deoxy-4-O-methyl-5-C-(2-propenyl)-3-0-[[(2-propynyloxy)amino]carbonyl]-.beta.-.-D-gulopyranosyl]oxy]-4-hydroxy-8-methyl-3-[1-[(2-propynyloxy)imino]ethyl]-2H-1-benzopyran-2-one
and 7-[[6-deoxy-4-O-methyl-5-C-(2-propenyl)-3-0-[[(2-propynyloxy)amino]carbonyl]-.beta.-.-D-gulopyranosyl]oxy]-4-hydroxy-3-[1-(methoxyimino) ethyl]-8-methyl-2H-1-benzopyran-2-one

STAGE A:

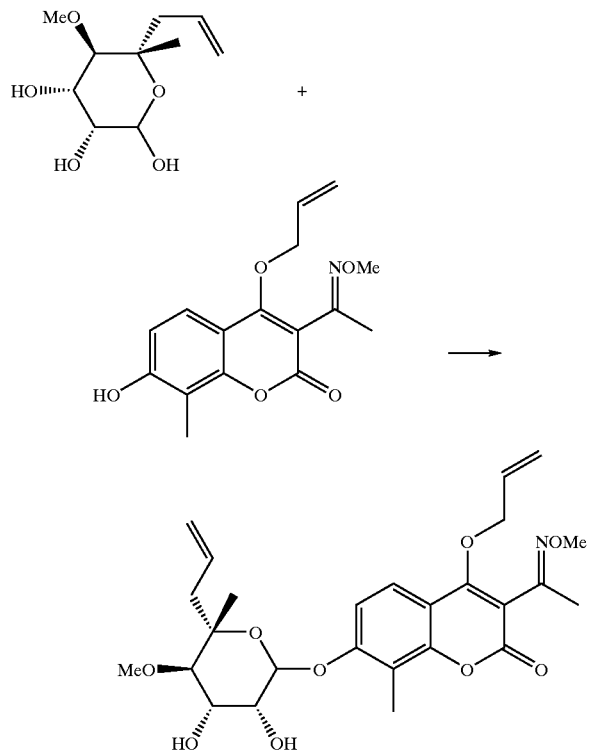

4.4 g of the product of preparation 4 in solution is dissolved in 100 ml of methylene chloride. 7.33 g of coumarine (7-hydroxy-3-[(methoxyimino)methyl]-8-methyl-4-(2-propenyloxy)-2H-1-benzopyran-2-one) prepared as indicated in preparation 8 of the international Patent Application WO 9747634 and 6.29 g of triphenylphosphine are added under argon at ambient temperature. The suspension is cooled down to 0° C. 3.73 ml of DEAD is added dropwise. The suspension is agitated for 1 hour is added at ambient temperature. A further 6.06 g of triphenylphosphine and at 0° C. 3.11 ml of DEAD are added. After 1 hour of agitation at ambient temperature, 50 ml of pentane is added to precipitate the reduced DEAD. The suspension is filtered, the filtrate is evaporated to dryness and purified on silica with the eluent mixture toluene at 3% then 6% isopropyl alcohol. 7.1 g of product is obtained. The product is filtered on silica 60 eluting with an ether/heptane mixture then with ether. 6.13 g of sought product is obtained.

STAGE B:

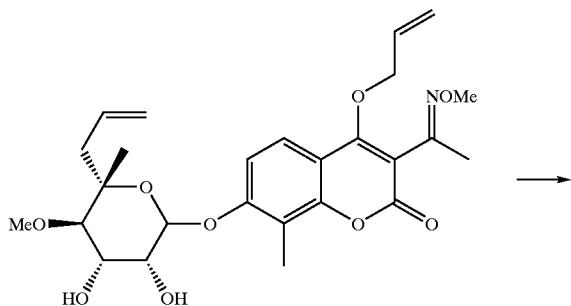

6 g of the product of the previous stage is dissolved in 75 ml of tetrahydrofurane. 3.86 g of carbonyldiimidazole is added and the reaction is heated for 1 hour under reflux. The reaction medium is diluted with 100 ml of heptane 1/ethyl acetate 2 mixture. The organic phase is washed with an oaueous solution of sodium hydrogen sulphate at 10%, dried over magnesium sulphate and evaporated to dryness. 4.94 g of sought product is obtained.

STAGE C:

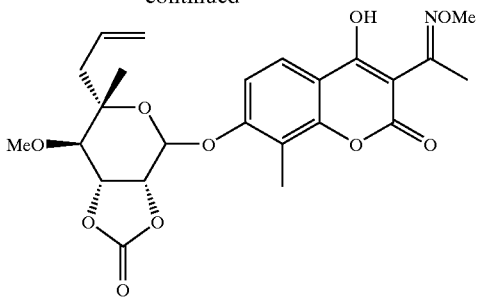

4.94 g of the product of the previous stage is dissolved in 120 ml of tetrahydrofurane. 8.44 ml of dilsopropylamine is added at 0° C., 1.05 g of palladium tetrakistriphenylphosphine. Agitation is carried out for 20 minutes at 0° C. The reaction medium is diluted with 50 ml of a heptane 1/ethyl acetate 2 mixture. The organic phase is washed with an aqueous solution of sodium hydrogen sulphate at 10%, dried over magnesium sulphate and evaporated to dryness. 5.5 g of crude product is obtained which is purified on silica eluting with a methylene chloride mixture with 2% acetone. 3.1 g of sought product is obtained.

STAGE D:

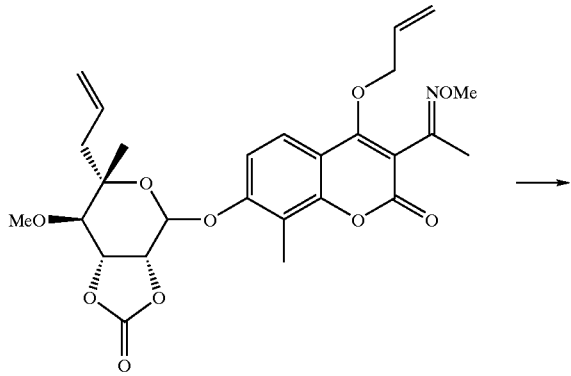

0.65 g of the product of the previous stage is dissolved in 6.5 ml of pyridine dried over potassium. 1.5 g of propargylhydroxylamine hydrochloride and 0.149 of lithium perchlorate are added at ambient temperature. Agitation is carried out at ambient temperature for 48 hours followed by diluting with a heptanellethyl acetate 2 mixture, and the organic phase is washed with a sodium hydrogen sulphate solution at 10%, dried over magnesium sulphate. 1.8 g of product is obtained which is purified by chromatography on silica eluting with the eluent mixture methylene chloride 80/terbutylmethylether 20.

200 mg of 3-isomer sought product and 500 mg is 2-isomer is obtained.

STAGE E:

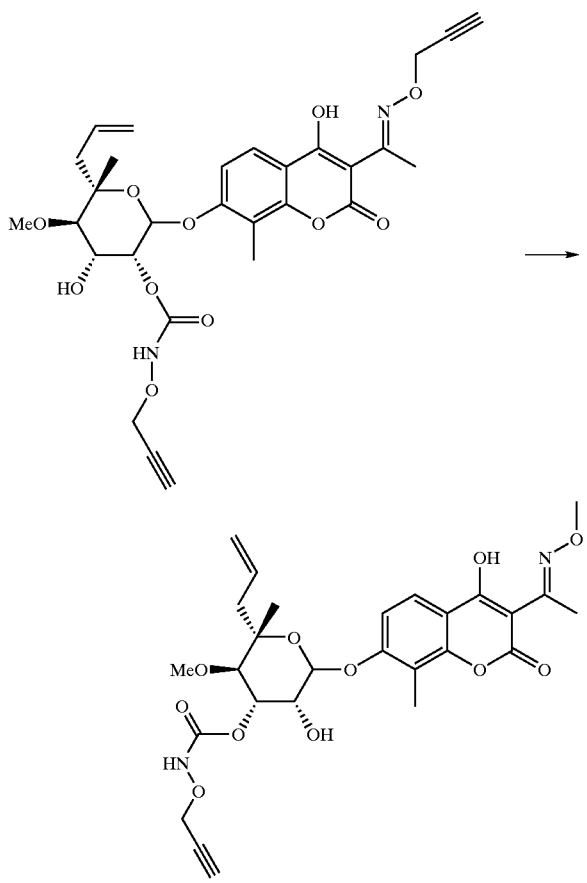

0.5 g of the 2-isomer obtained in the previous stage is dissolved in 10 ml of methylene chloride under an argon atmosphere. 100 µl of DBU is added. Agitation is carried out for 24 hours at ambient temperature followed by diluting in 50 ml of a heptane 1/ethyl acetate 3 mixture and the organic phase is washed with a 1 M solution of sodium dihydrogen sulphate, dried over magnesium sulphate and evaporated to dryness. The product obtained previously is dissolved in 5 ml of ethanol. 0.72 g of methylhydroxylamine hydrochloride and 0.94 g of sodium acetate are added at ambient temperature. The reaction medium is agitated for 5 hours at ambient temperature followed by diluting in 50 ml of heptane 1/ethyl acetate 3 mixture and the organic phase is washed with a 1 M solution of sodium dihydrogen sulphate, dried over magnesium sulphate and evaporated to dryness. 0.45 g of crude product is obtained which is purified by chromatography on silica with the eluent mixture methylene chloride 80/20 terbutylmethylether 20.

100 mg of sought product is obtained.

Preparation 5

STAGE A:

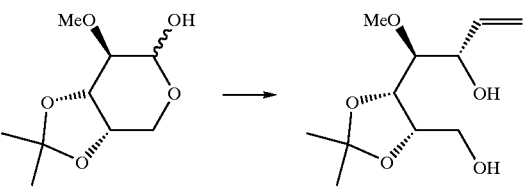

20.4 g of 2-0-methyl-3,4-0(1-methylethylidene)L-arabinose is dissolved under argon in 250 ml of tetrahydrofurane. 100 ml of a 1 M solution of vinylmagnesium bromide in tetrahydrofurane then 200 ml of a 1.7 M magnesium chloride solution in tetrahydrofurane; 0.34 moles are added at 0° C. under argon. The solution is agitated for 1 hour at ambient temperature. The reaction medium is cooled down to –15° C. and diluted with 100 ml of heptane. In order to neutralize the excess magnesium, 300 ml of a mixture of 20% of a molar aqueous solution of sodium dihydrogen phosphate in tetrahydrofurane is added. The magnesium salts precipitate. 200 ml of a heptane 1/ethyl acetate 2 mixture and 150 ml of a 10% solution of sodium hydrogen sulphate are added. The organic solution is dried over magnesium sulphate and evaporated to dryness. 19.3 g of sought product is obtained.

Yield: 83%

STAGE B:

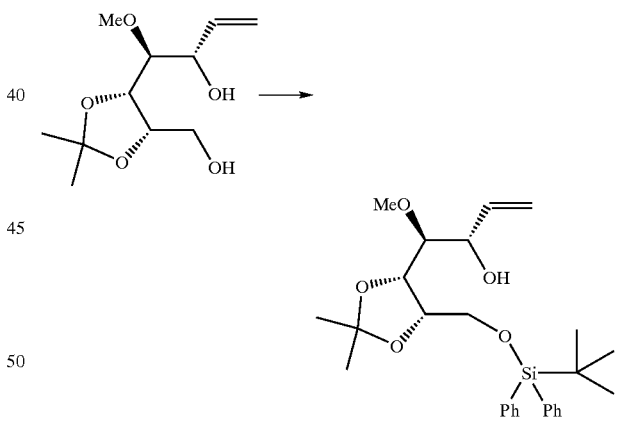

19.3 g of the product of the previous stage is dissolved in 150 ml of dimethylformamide. 10.8 g of imidazole is added, then at 0° C. under argon, 23.4 ml of diphenylterbutylsilyl chloride is added dropwise for 30 minutes. The solution is agitated for 30 minutes at 0° C. The reaction medium is diluted with 400 ml of a heptane 1/ethyl acetate 2 mixture. The organic phase is washed with a 1 M aqueous solution of sodium dihydrogen phosphate, dried over magnesium sulphate and evaporated to dryness. 30.2 g of resin product is obtained which is purified by chromatography on silica eluting with the heptane 4:ethyl acetate 1 mixture. 30.2 g of sought product is obtained. Yield: 77%

STAGE C:

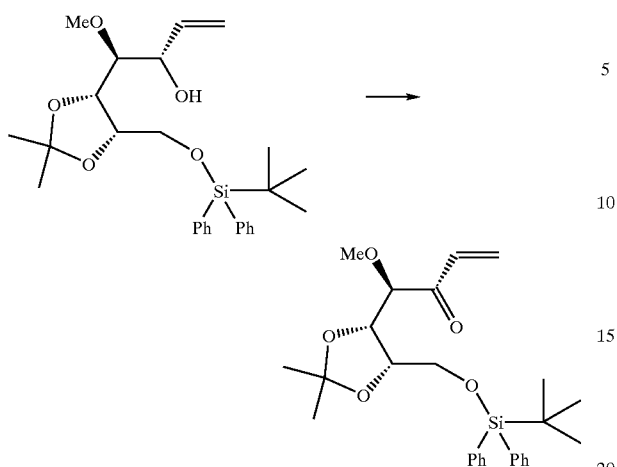

19.1 g of pyridinium chlorochromate is dissolved in 250 ml of methylene chloride. Then 40 g of 4 Å molecular sieve is added. 28.19 g of the product of the previous stage in solution in 100 ml of methylene chloride is introduced into this suspension in one go. After 4 hours of agitation at ambient temperature, the reaction is finished. The reaction medium is filtered. The filtrate is evaporated to dryness. The product obtained is chromatographed on silica eluting with a heptane/ethyl acetate 6-1 mixture. 10.5 g of sought product is obtained. Yield 36%.

STAGE D:

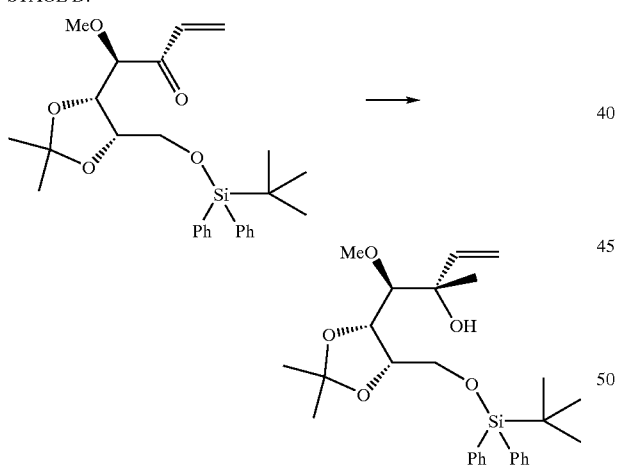

10 g of the product of the previous stage is dissolved in 100 ml of tetrahydrofurane. 14 ml of a 3 M solution of methylmagnesium bromide in ether is added dropwise under argon at −5° C. Agitation is carried out for 30 minutes at 0° C., the excess magnesium is neutralized with an aqueous solution of sodium hydrogen sulphate at 10%. 200 ml of a heptane 1/ethyl acetate 2 mixture is added. The organic phase is washed with 200 ml of a molar aqueous solution of sodium dihydrogen phosphate, dried over magnesium sulphate and evaporated to dryness. The crude product is purified on silica eluting with a heptane 4/ethyl acetate 1 mixture. The product obtained is impasted in pentane. 2.76 g of sought product is obtained.

Yield 27%

STAGE E:

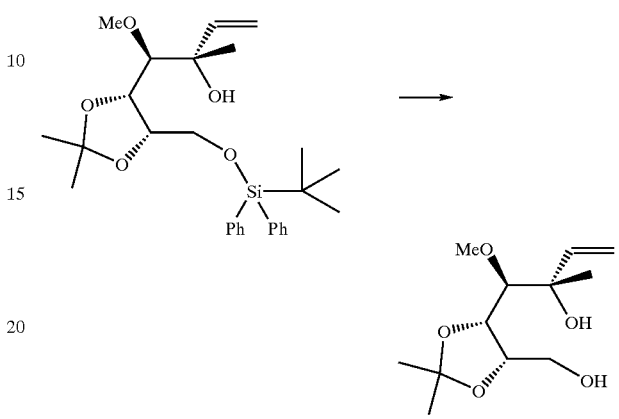

2.79 g of the product of the previous stage is dissolved in 15 ml of tetrahydrofurane. 11.8 ml of a molar solution of tetrabutylammonium fluoride in tetrahydrofurane is added dropwise under argon at 0° C. Agitation is carried out for 1 hour at ambient temperature is added. 200 ml of a heptane 1/ethyl acetate 2 mixture. The organic phase is washed with 200 ml of a molar aqueous solution of sodium dihydrogen phosphate, dried over magnesium sulphate and evaporated to dryness. The crude product is purified by chromatography of silica eluting with a methylene chloride mixture with 5% methanol. 1.2 g of sought product is obtained. Yield: 86%

STAGE F:

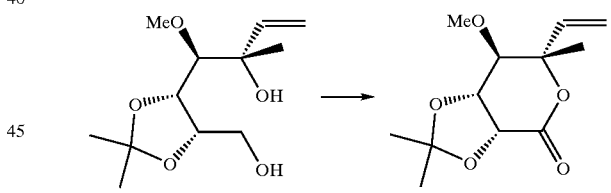

1.2 g of the product of the previous stage is dissolved in 12.5 ml of methylene chloride. 6.67 ml of triethylamine and 12.5 ml of dimethylsulphoxide stored on molecular sieve are added under argon at 0° C. The solution is cooled down to approximately 5° C. with an ice-water bath and 2.39 g of pyridine sulphurtrioxide is added by fractions without the temperature exceeding 15° C. After 1 hour of agitation at ambient temperature, the reaction is terminated. Agitation is carried out for 1 hour at ambient temperature. The reaction medium is poured into 100 ml of a molar aqueous solution of sodium dihydrogen phosphate, the aqueous phase is extracted twice with a heptane 1/ethyl acetate 2 mixture. The organic phase is washed with water, dried over magnesium sulphate and evaporated to dryness. The product obtained is impasted in pentane. 0.75 g of sought product is obtained. Yield: 59%

STAGE G:

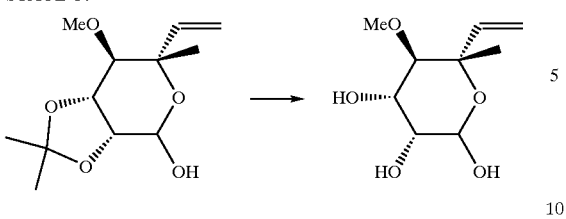

0.73 g of the product of the previous stage is dissolved in 30 ml of tetrahydrofurane. 2.5 ml of a 1.5 M solution of DIBAL in toluene is added under argon at −6° C.

Agitation is carried out for 1 hour 30 minutes at −6° C. The reaction medium is poured into a 1M solution of sodium potassium tartrate; the aqueous phase is extracted with a heptane 1/ethyl acetate 2 mixture. The organic phase is washed with an aqueous solution of sodium hydrogen sulphate at 10%, dried over magnesium sulphate and evaporated to dryness. The product obtained is impasted in pentane. 0.95 g of sought product is obtained. Quantitative yield.

STAGE H:

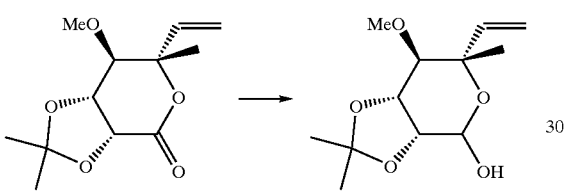

0.9 g of the product of the previous stage is emulsified in 5 ml of a solution of sulphuric acid at 0.05 N. After 1 hour of heating at 70° C., the reaction is terminated. The reaction medium is left to return to ambient temperature, then extracted with pentane and the aqueous phase is neutralized with 0.1 g of barium carbonate. The suspension is acitated for one hour at ambient temperature (pH=7), then filtered and evaporated to dryness. In order to dry the product, two distillations are carried out with toluene, followed by solubilizing in methylene chloride, drying the solution over magnesium sulphate and evaporating to dryness. 0.5 g of sought product is obtained.

Yield 86%.

EXAMPLE 7

7-[[6-deoxy-5-C-ethenyl-4-O-methyl-3-O-[[(2-propynyloxy)amino]carbonyl]-.beta.-D-gulopyranosyl]oxy]-4-hydroxy-3-[1-(methoxymino)ethyl]-8-methyl-2H-1-benzopyran-2-one

STAGE A:

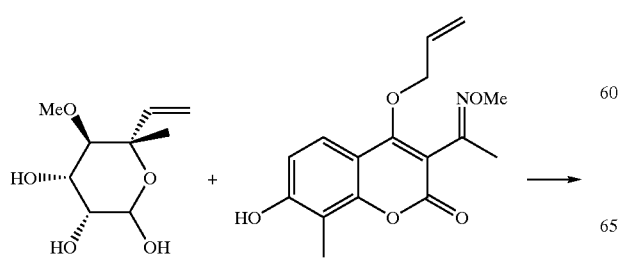

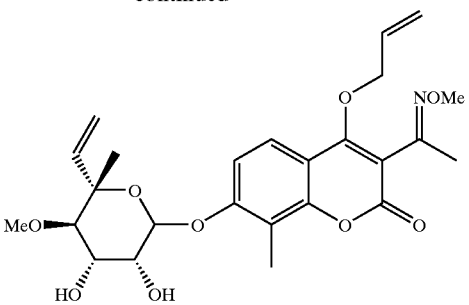

0.5 g of the product of preparation 5 is dissolved in 17 ml of methylene chloride. 0.89 g of coumarine prepared as indicated in the International Patent Application WO9747634 and 0.76 g of triphenylphosphine are added at ambient temperature under argon. The suspension is cooled down to 0° C., 0.45 ml of DEAD is added dropwise. The suspension is agitated for 1 hour at ambient temperature. 0.63 g of triphenylphosphine is added again and at 0° C., 0.37 ml of DEAD. A yellow solution is obtained. After 1 hour of agitation at ambient temperature, 10 ml of pentane is added to precipitate the reduced DEAD. The suspension is filtered, the filtrate is evaporated to dryness and purified by chromatography on silica with the eluent mixture toluene 97/isopropyl alcohol 3 (the elution is finished with 6%). The product obtained in a mixture is then filtered on silica 60 eluting with a heptane 1/ether 2 mixture then ether. 0.55 g of white crystals is obtained. Yield: 47%.

STAGE B:

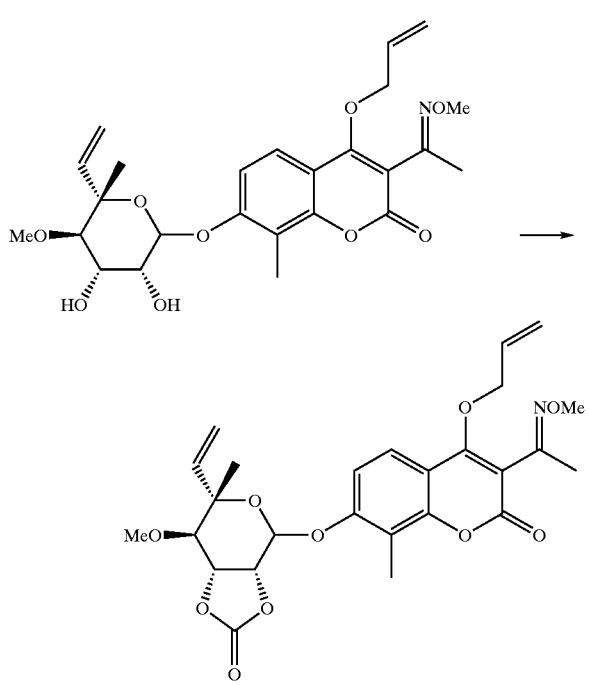

0.55 g of the product of the previous stage is dissolved in 7 ml of tetrahydrofurane. 0.364 g of carbonyldiimidazole is added and the reaction mixture is heated for 1 hour under reflux. The reaction medium is diluted with 40 ml of heptane 1/ethyl acetate 2 mixture. The organic phase is washed with 50 ml of an aqueous solution of sodium hydrogen sulphate at 10%, dried over magnesium sulphate and evaporated to dryness. 0.5 g of sought product is obtained.

Yield: 88%

STAGE C:

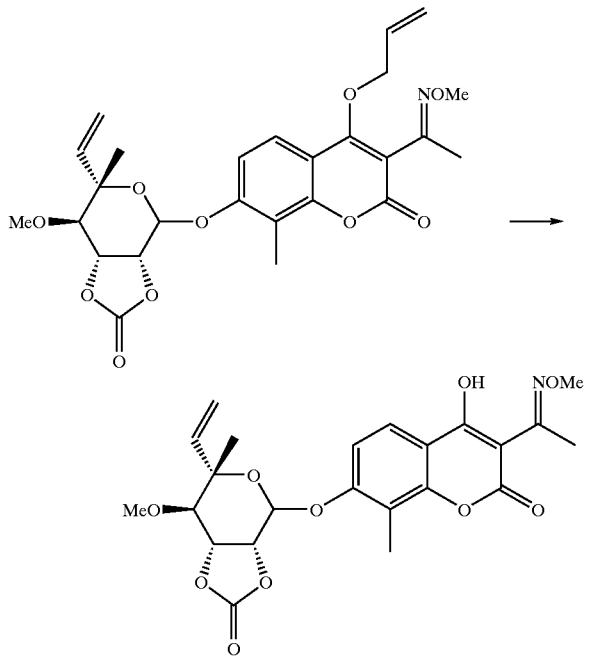

0.5 g of the product of the previous stage is dissolved in 12 ml of tetrahydrofurane. 0.82 ml of diisopropylamine and at 0° C., 0.11 g of palladium tetrakistriphenylphosphine (0.1 equivalent), are added. Agitation is carried out for 20 minutes at 0° C. The reaction medium is diluted with 50 ml of a heptane 1/ethyl acetate 2 mixture. The organic phase is washed with 50 ml of an aqueous solution of sodium hydrogen sulphate at 10%, dried over magnesium sulphate and evaporated to dryness. 0.58 g of crude product is obtained which is purified by chromatography on silica eluting with a heptane 3/ethyl acetate 1 mixture. 0.257 g of sought product is obtained. Yield: 57%.

STAGE D:

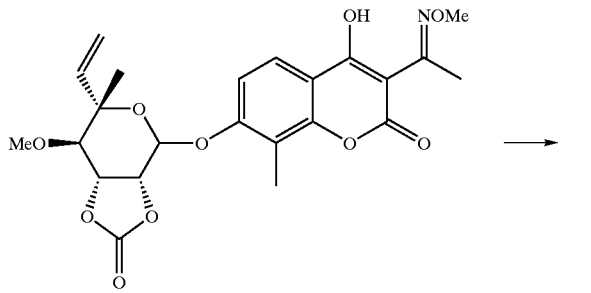

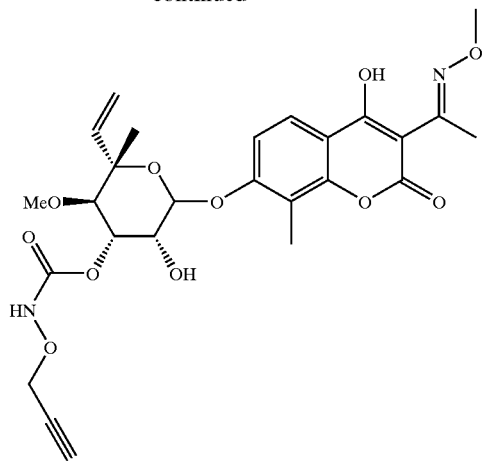

0.257 g of the product from the previous stage is dissolved in 2.5 ml of pyridine dried over potassium. 0.58 g of propargylhydroxylamine hydrochloride and 0.057 g of lithium perchlorate are added. The reaction medium is agitated for 48 hours at ambient temperature followed by diluting with a heptane 1/ethyl acetate 2 mixture, and the organic phase is washed with a solution of sodium hydrogen sulphate at 10%, dried over magnesium sulphate. 0.28 g of sought product is obtained. The crude product obtained is dissolved in 5 ml of ethanol, 0.45 g of methylhydroxylamine hydrochloride and 0.58 g of sodium acetate are added. The reaction medium is agitated for 5 hours at ambient temperature followed by diluting with a heptane 1/ethyl acetate 2 mixture and the organic phase is washed with a sodium dihydrogen phosphate (1 M) solution, dried over magnesium sulphate and evaporated to dryness. 0.3 g of crude product is obtained which is purified by chromatography on silica eluting with a methylene chloride 80/ethyl acetate 19/acetic acid 1 mixture. 0.090 g of sought product is obtained. Yield: 31%.

Preparation 6

STAGE A:

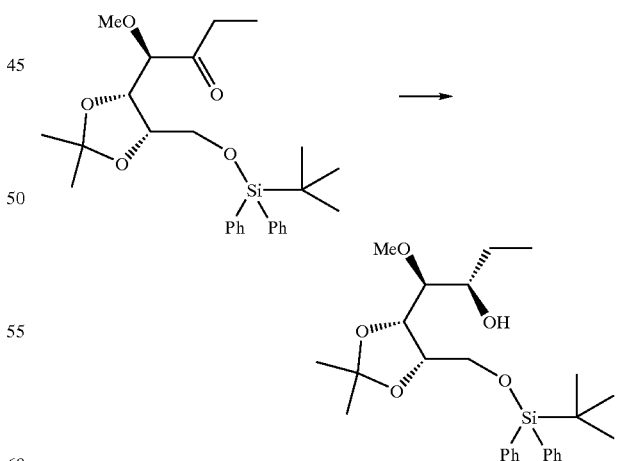

10.5 g is dissolved in 110 ml of tetrahydrofurane. 329 ml of a 0.135 M solution of zinc tetraborohydride in ether is added under argon at −6° C. Agitation is maintained for 30 minutes without an ice bath, the reaction is then terminated. A solution of sodium dihydrogen phosphate (M) is added. The aqueous phase is extracted with a heptane 1/ethyl acetate 2 mixture. The organic phase is dried over magnesium sulphate and evaporated to dryness. 10.5 g of sought product is obtained which is purified by chromatography eluting with a heptane 4/ethyl acetate 1 mixture. 8.75 g of sought product is obtained. Yield: 83%

STAGE B:

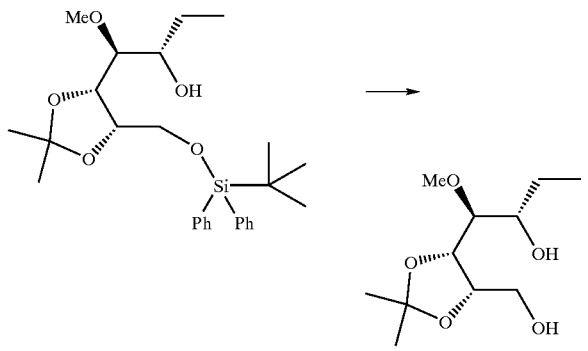

8.75 g of the product of the previous stage is dissolved in 100 ml of tetrahydrofurane. 37 ml of a molar solution of tetrabutylammonium fluoride in tetrahydrofurane is added under argon at 0° C. After 30 minutes of agitation at 0° C., 200 ml of a heptane 1/ethyl acetate 2 mixture is added. The organic phase is washed with 200 ml of a molar aqueous solution of sodium dihydrogen phosphate, dried over magnesium sulphate and evaporated to dryness. The crude product (10.5 g) is purified by chromatography eluting the methylene chloride with 20% of acetone mixture on silica. 3.6 g of sought product is obtained.
Yield: 78%.

STAGE C:

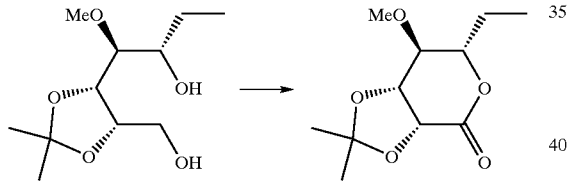

3.57 g of the product of the previous stage is dissolved in 38 ml of methylene chloride. 20.5 ml of triethylamine and 38 ml of dimethylsulphoxide are added under araon at ambient temperature. The solution is cooled down to approximately 5° C. and 7.6 g of pyridine sulphur trioxide is added without the temperature exceeding 15° C. Agitation is carried out for 2 hours. The reaction medium is poured into 500 ml of a molar aqueous solution of sodium dihydrogen phosphate, the aqueous phase is extracted twice with a heptane 1/ethyl acetate 2 mixture. The organic phase is washed twice with 500 ml of water, dried over magnesium sulphate and evaporated to dryness. The crude product crystallizes and is impasted in pentane. 1.92 g of sought product is obtained.
Yield: 56%

STAGE D:

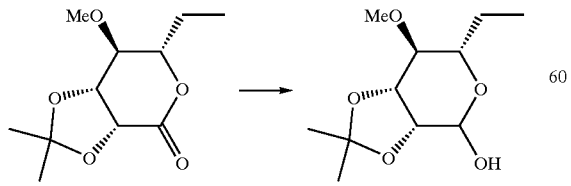

1.9 g of the product of the previous stage is dissolved in 10 ml of tetrahydrofurane. 6.66 ml of 1.5 M solution of DIBAL in toluene is added under argon at 0° C. Agitation is carried out for 1 hour 30 minutes. The reaction medium is poured into 100 ml of a 1M solution of sodium potassium tartrate; the aqueous phase is extracted with a heptane 1/ethyl acetate 2 mixture. The organic phase is washed with 150 ml of an aqueous solution of sodium hydrogen sulphate at 10%, dried over magnesium sulphate and evaporated to dryness.
1.9 g of sought product is obtained.
Yield: Quantitative

STAGE E:

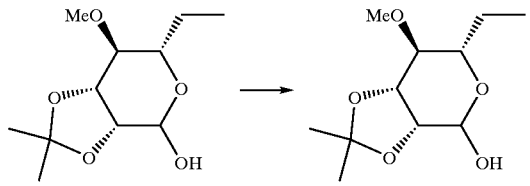

1.95 g of the product of the previous stage is emulsified in 11.5 ml of a sulphuric acid solution at 0.05 N followed by heating for 1 hour 30 minutes at 70° C. and left to return to ambient temperature. The reaction medium is neutralized with 0.3 g of barium carbonate. The suspension is agitated for one hour at ambient temperature (pH=7), then filtered and evaporated to dryness. In order to dry the product, two distillations with toluene are carried out. After drying (overnight at 40° C. in the presence of $P_2O_5$), 1.2 g of sought product is obtained.
Yield: Quantitative

EXAMPLE 8

7-[(6-deoxy-6-C-methyl-4-O-methyl-3-O-[[(2-propynyloxy)amino]carbonyl]-.alpha.-L-mannopyranosyl)oxy]-4-hydroxy-8-methyl-3-[1-[(2-propynyloxy)imino]ethyl]-2H-1-benzopyran-3-yl]-2-one 7-[(6-deoxy-6-C-methyl-4-O-methyl-3-O-[[(2-propynyloxy)amino]carbonyl]-.alpha.-L-mannopyranosyl)oxy]-4-hydroxy-3-[1-(methoxyimino)ethyl]-8-methyl-2H-1-benzopyran-3-yl]2-one

STAGE A:

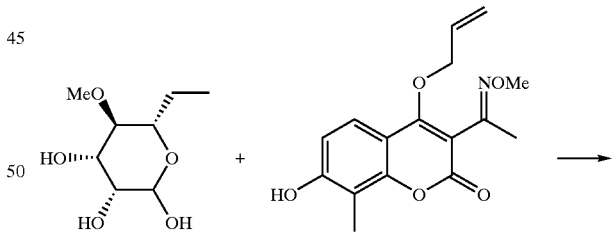

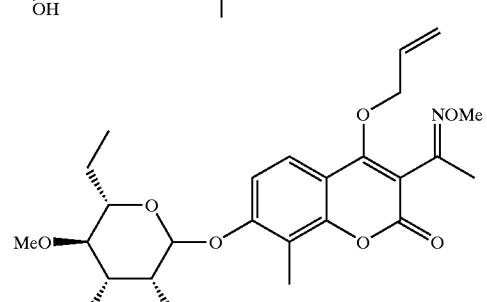

1.16 g of the product of preparation 6 is dissolved in 25 ml of methylene chloride. 2.19 g of coumarine 7-hydroxy- 3[(methoxyimino)methyl]-8-methyl-4-(2-propenyloxy)-2H-1-benzopyran-2-one prepared as indicated in the International Patent Application W09747634 and 1.89 g of triphenylphosphine are added under argon at ambient temperature. The suspension is cooled down to 0° C., 1.12 ml of DEAD is added dropwise. The suspension is agitated for 1 hour at ambient temperature. A further 1.58 g of triphenylphosphine and, at 0° C., 0.93 ml of DEAD are added. After 1 hour of agitation at ambient temperature, 50 ml of pentane is added to precipitate the reduced DEAD. The suspension is filtered, the filtrate is evaporated to dryness and purified by chromatography on silica eluting with a toluene mixture with 3% isopropyl alcohol. 0.870 g of white crystals and 0.850 g of a mixture containing traces of reduced DEAD are obtained. The product is filtered rapidly on 100 g of silica 60 eluting with ether. 0.4 g of sought product is obtained.

Total weight: 1.27 g. Yield: 44%

STAGE B:

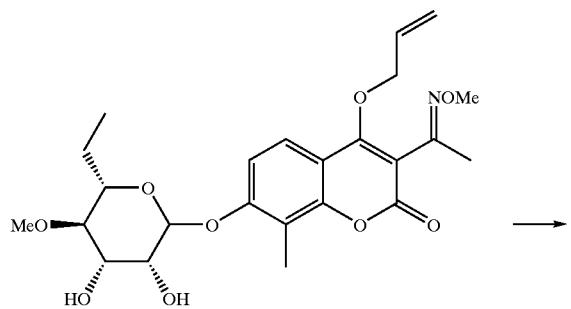

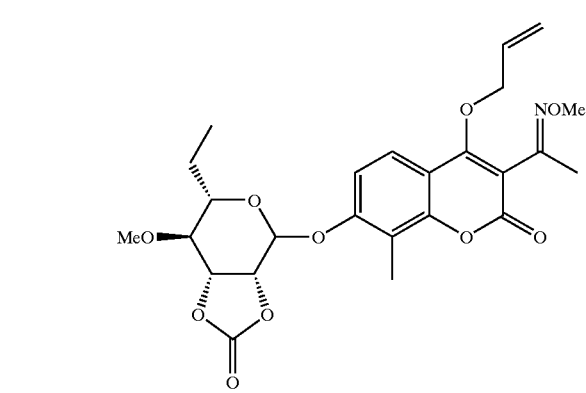

1.27 g of the product of the previous stage is dissolved in 10 ml of tetrahydrofurane. 0.85 g of carbonyldiimidazole is added followed by heating for 1 hour under reflux. The reaction medium is diluted with 50 ml of a heptane 1/ethyl acetate 2 mixture. The organic phase is washed twice with 50 ml of an aqueous solution of sodium hydrogen sulphate at 10%, dried over magnesium sulphate and evaporated to dryness. 1.41 g of sought product is obtained.

Yield: Quantitative

STAGE C:

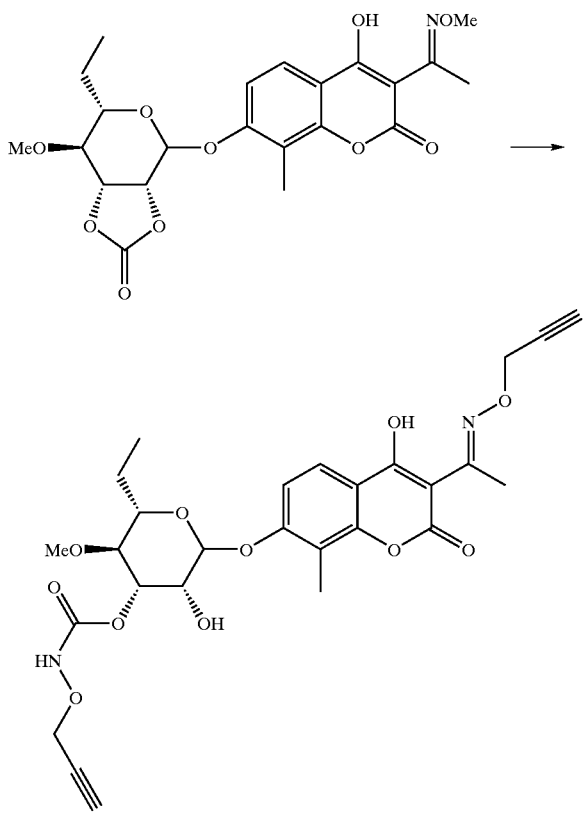

0.6 g of the product of the previous stage is dissolved in 6.5 ml of pyridine dried over potassium. 1.5 g of propargylhydroxylamine hydrochloride and 0.149 of lithium perchlorate are added at ambient temperature. Agitation is carried out for 48 hours at ambient temperature followed by dilution with a heptane 1/ethyl acetate 2 mixture and the organic phase is washed with a sodium hydrogen sulphate solution at 10%, dried over magnesium sulphate. 1.8 g of product is obtained which is chromatographed on silica eluting with a methylene chloride 80/ethyl acetate 19/acetic. acid 1 mixture. 186 mg of isomer-3 sought product is obtained, 400 mg of isomer-2.

Yield: 74% opening of the carbonate of which 30% is isomer-3.

STAGE D:

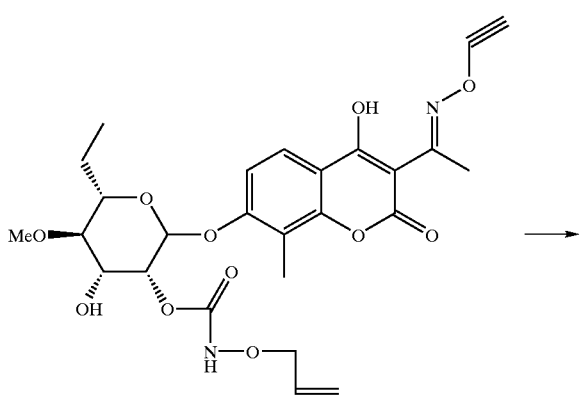

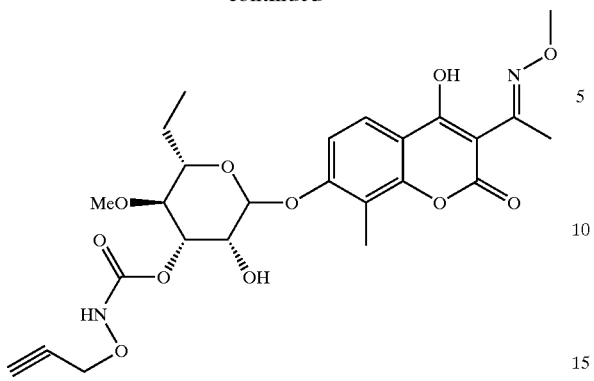

0.4 g of the product of the previous stage (isomer-2) is dissolved in 10 ml of methylene chloride. 100 µl of DBU is added. Agitation is carried out for 24 hours at ambient temperature followed by diluting with a heptane 1/ethyl acetate 2 mixture and the organic phase is washed with a 1 M solution of sodium dihydrogen phosphate, dried over magnesium sulphate and evaporated to dryness. In a 100 ml flask, 0.4 g of the mixture previously obtained is dissolved in 10 ml of ethanol. 0.59 g of methylhydroxylamine hydrochloride and 0.76 g of sodium acetate are added at ambient temperature. The dreaction medium is agitated for 5 hours at ambient temperature followed by diluting with a heptane 1/ethyl acetate 2 mixture, and the organic phase is washed with a 1 M solution of sodium dihydrogen phosphate, dried over magnesium sulphate and evaporated to dryness. 0.45 g of crude product is obtained which is purified on silica:with a methylene chloride 80/ethyl acetate 19/acetic acid 1 eluent mixture. Only the expected isomer-3 is isolated. 0.140 g of sought product is obtained.

Yield: 37%

Preparation 7

STAGE A:

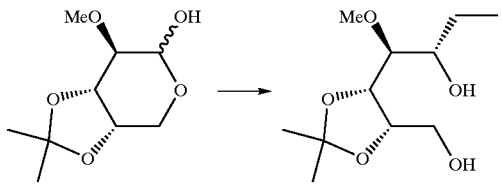

26.8 g of product is dissolved under argon in 250 ml of tetrahydrofurane. 400 ml of a 1 M solution of ethylmagnesium bromide in tetahydrofurane is added dropwise at 0° C. under argon. The solution is agitated for 2 hours at ambient temperature. The reaction medium is cooled down to 0° C. and is diluted with 100 ml of heptane. In order to neutralize the excess magnesium, 300 ml of a molar aqueous solution of sodium dihydrogen phosphate is added dropwise. Magnesium salts precipitate. 200 ml of a heptane 1/ethyl acetate 2 mixture and 150 ml of a 10% solution of sodium hydrogen sulphate are added. The organic solution is dried over magnesium sulphate and evaporated to dryness.

29 g of product is obtained which is chromatographed on silica eluting with a heptane 1/ethyl acetate 4 mixture. 17 g of sought product is obtained. Yield 52%.

STAGE B:

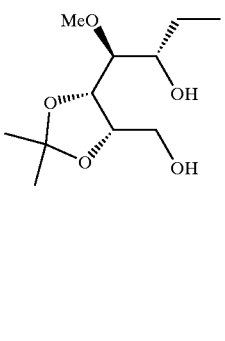

16.7 g of the product of the previous stage is dissolved under argon in 150 ml of dimethylformamide. 10.07 g of imidazole is added then 19.23 ml of diphenylterbutylsilyl chloride is added dropwise at 0° C. under argon over 30 minutes.

The solution is agitated for 1 hour 30 minutes at ambient temperature.

The reaction medium is diluted with 400 ml of heptane 1/ethyl acetate 2 mixture. The organic phase is washed with a molar aqueous solution of sodium dihydrocen phosphate, dried over magnesium sulphate and evaporated to dryness. 38 g of product is obtained which is purified by chromatography on silica eluting with a methylene chloride mixture with 10% of acetone. 33.23 g of sought product is obtained.

Yield: Quantitative

STAGE C:

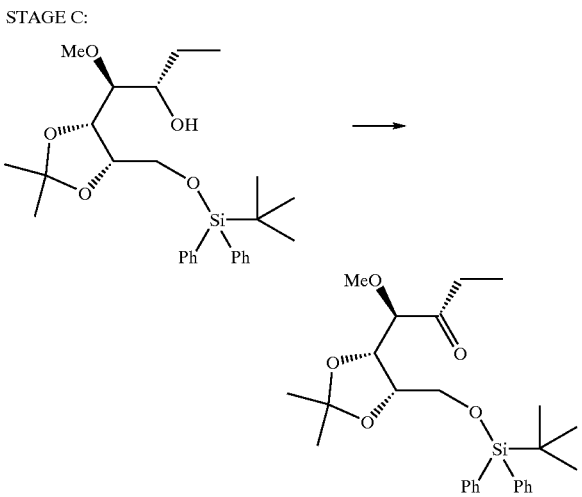

22.57 g of pyridinium chlorochromate 0.104 moles is suspended in 300 ml of methylene chloride. Then 110 g of molecular 4 Å sieve is added. 33 g of the product of the previous stage in solution in 100 ml of methylene chloride is introduced into this suspension. After 3 hours of agitation at ambient temperature, the suspension is filtered. The filtrate is evaporated to dryness. The-residue obtained (35 g) is purified on silica with the eluent mixture heptane 4/ethyl acetate 1. 27 g of sought product is obtained. Yield 83%.

STAGE D:

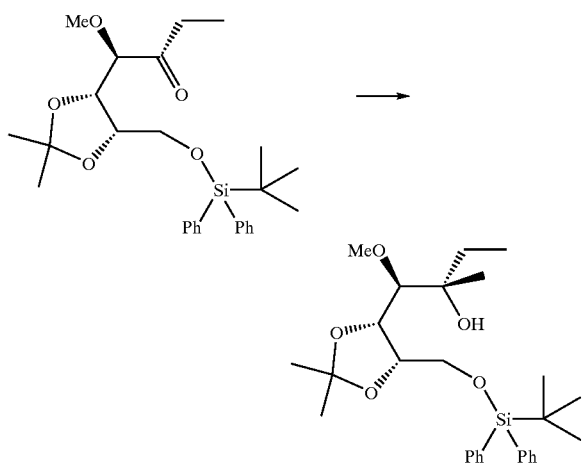

16.5 g of the product of the previous stage is dissolved in 150 ml of tetrahydrofurane. 17.52 ml of a 3M solution of methylmagnesium bromide in ether is added dropwise under argon at −5° C. Agitation is carried out for 1 hour at ambient temperature. The excess magnesium is neutralized at 0° C. with a molar aqueous solution of sodium dihydrogen phosphate. 200 ml of a heptane 1/ethyl acetate 2 mixture is added. The organic phase is washed with 200 ml of a molar aqueous solution of sodium dihydrogen phosphate, dried over magnesium sulphate and evaporated to dryness. The product obtained is impasted in pentane.

14.85 g of sought product is obtained. Yield: 87%

STAGE E:

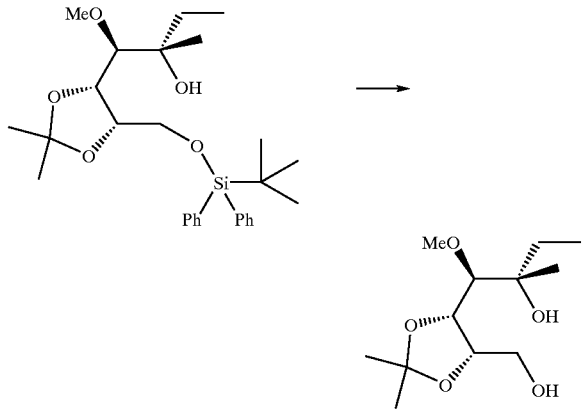

14.85 g of the product of the previous stage is dissolved in 150 ml of tetrahydrofurane. 33 ml of a molar solution of tetrabutylammonium fluoride in tetrahydrofurane is added dropwise under argon at 0° C. After 30 minutes of agitation at ambient temperature, the reaction is terminated. 200 ml of a heptane 1/ethyl acetate 2 mixture is added. The organic phase is washed with 200 ml of a molar aqueous solution of sodium dihydrogen phosphate, dried over magnesium sulphate and evaporated to dryness. The crude product it purified on silica eluting with a methylene chloride mixture with 15% of acetone then with 30% of acetone. 7.85 g of sought product is obtained.

Yield: Quantitative

STAGE F:

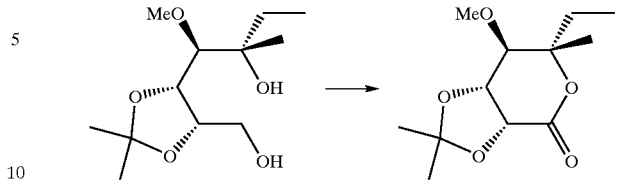

7.85 g of the product of the previous stage is dissolved in 82.5 ml of methylene chloride. 44.5 ml of triethylamine and 82.5 ml of dimethylsulphoxide stored on molecular sieve are added under argon at ambient temperature. The solution is cooled down to approximately 5° C. with an ice water bath and 15.8 g of pyridine sulphur trioxide is added by fractions without the temperature exceeding 15° C. Agitation is carried out for 1 hour. The reaction medium is poured into 1 litre of a molar aqueous solution of sodium dihydrogen phosphate, the aqueous phase is extracted with a heptane 1/ethyl acetate 2 mixture. The organic phase is washed with water, dried over magnesium sulphate and evaporated to dryness.

The product obtained is impasted in pentane.

5.77 g of sought product is obtained.

Yield 80%.

STAGE G:

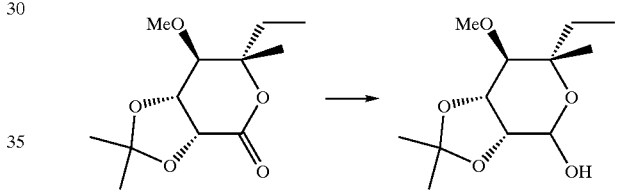

5.46 g of the product of the previous stage is dissolved in 25 ml of tetrahydrofurane. 16.7 ml of a 1.5 M solution of DIBAL in toluene is added under argon at 0° C. Agitation is carried out for 1 hour 30 minutes at 0° C. The reaction medium is poured into 250 ml of a 1 M solution of sodium potassium tartrate; the aqueous phase is extracted with a heptane 1/ethyl acetate 2 mixture. The organic phase is washed with 150 ml of an aqueous solution of sodium sulphate at 10%, dried over magnesium sulphate and evaporated to dryness. 5.5 g of sought product is obtained. Yield: Quantitative

STAGE H:

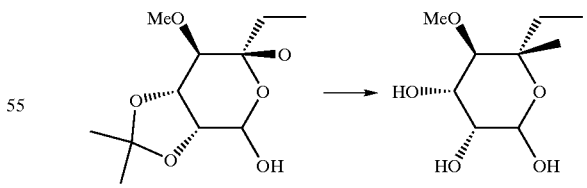

5.5 g of the product of the previous stage is emulsified in 32 ml of a solution of sulphuric acid at 0.05 N. After one hour 30 minutes of heating at 70° C., the reaction is terminated. The reaction medium is left to return to ambient temperature and is neutralized with 0.6 g of barium carbonate; the suspension is agitated for one hour at ambient temperature (pH=7), then filtered on miliporous filter paper and evaporated to dryness. In order to dry the product, two

EXAMPLE 9

7-[(6-deoxy-5-C-ethyl-4-O-methyl-.beta.-D-gulopyranosyl)oxy]-4-hydroxy-8-methyl-3-[1-[(2-propynyloxy)imino]ethyl]-2H-1-benzopyran-2-one (2-propynyloxy)-carbamic 3'-ester acid

7-[(6-deoxy-5-C-ethyl-4-O-methyl-.beta.-D-gulopyranosyl)oxy]-4-hydroxy-3-[1-(methoxyimino]ethyl]-8-methyl-2H-1-benzopyran-2-one(2-propynyloxy)-carbamic 3'-ester acid

7-[(6-deoxy-5-C-ethyl-4-O-methyl-.beta.-D-gulopyranosyl)oxy]-3-[1-(ethoxyimino)ethyl]-4-hydroxy-8-methyl-2H-1-benzopyran-2-one (2-propynyloxy)-carbamic 3'-ester acid

STAGE A:

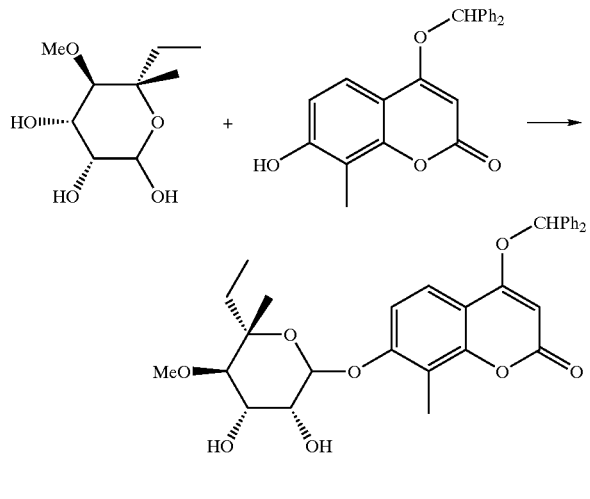

4.8 g of the product of preparation 7 is dissolved in 100 ml of methylene chloride. 9.98 g of coumarine and 7.23 g of triphenylphosphine are added at ambient temperature under argon. The suspension is cooled down to 0° C., 4.34 ml DEAD is added dropwise. The slightly yellow suspension is agitated for 1 hour at ambient temperature. A further 6 g of triphenylphosphine and at 0° C. 3.57 ml of DEAD are added. A yellow solution is obtained. After 1 hour of agitation at ambient temperature, 50 ml of pentane is added in order to precipitate the reduced DEAD. the suspension is filtered, the filtrate is evaporated to dryness and purified on 1.750 kg of silica 60 with an eluent mixture of toluene at 3% then 6% isopropyl alcohol. 10 g of white crystals containing traces of reduced DEAD is obtained. The product is filtered rapidly on silica 60 with an eluent mixture heptane 1/ethyl acetate 2 in order to eliminate the reduced DEAD, then with a methylene chloride 95/methanol 5 mixture in order to obtain 7.3 g of expected product. Yield: 58%

STAGE B:

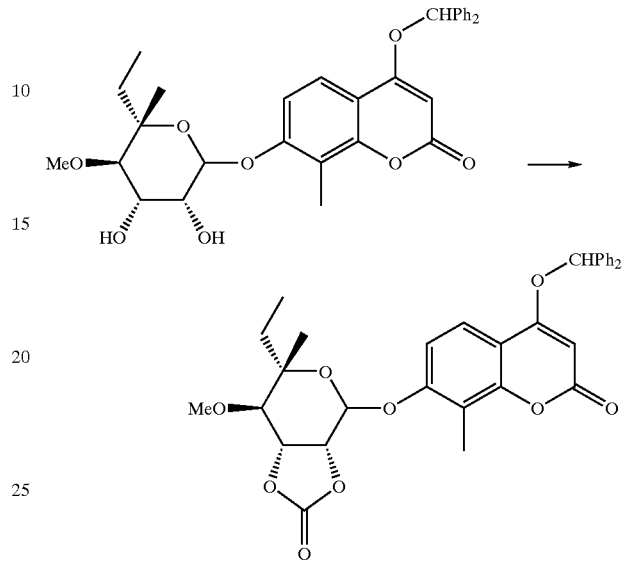

7.2 g of the product of the previous stage is introduced into 100 ml of TFF. 4.41 g diimidazole carbonate is added followed by heating for one hour under reflux. The reaction medium is poured into 150 ml of a hydrogen phosphate solution at 10% and extracted with a mixture of hexane,ethyl acetate followed by drying, and 7.1 g of sought product is obtained.

STAGE C:

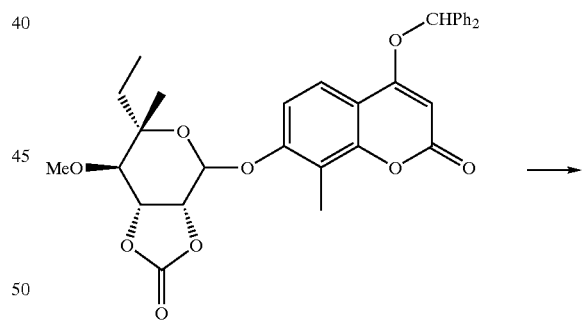

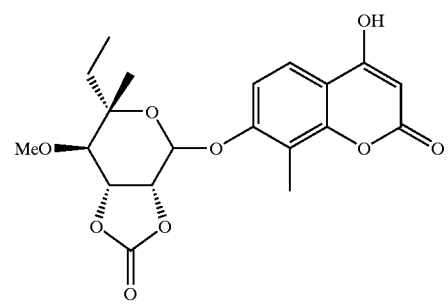

7.1 g of product is dissolved in 100 ml of tetrahydrofurane. 0.7 g of palladium on carbon is added followed by subjecting to a hydrogen atmosphere. After 3 hours of agitation, the reaction is terminated. The reaction medium is filtered and the filtrate is evaporated to dryness. The product is recrystallized in an ether/pentane mixture.

4.75 g of sought product is obtained.

Yield: 95%

STAGE D:

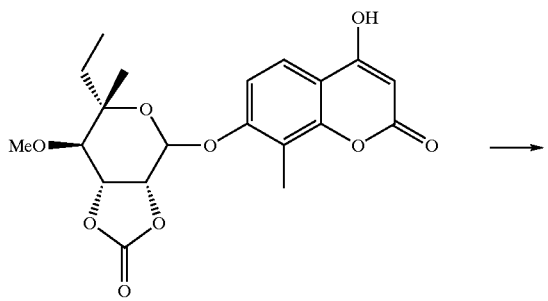

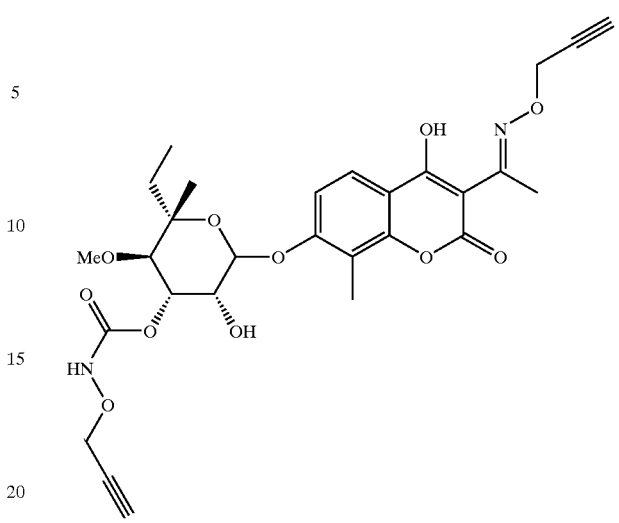

1.5 g of product obtained in the previous stage is dissolved in 25 ml of methylene chloride. 0.99 g of dimethylaminopyridine and dropwise under argon at 0° C., 0.38 ml of acetic anhydride are added. After 30 minutes of agitation at 0° C., 95 μl of acetic anhydride and 0.225 g of dimethylaminopyridine are added. Agitation is carried out for 45 minutes. The reaction medium is diluted with 100 ml of heptane 1/ethyl acetate 2 mixture. The organic phase is washed twice with 150 ml of a 1 M acueous solution of sodium dihydrogen phosphate, dried over magnesium sulphate and evaporated to dryness. The expected product is isolated. 1.56 g of sought product is obtained.

Yield: 93%

STAGE E:

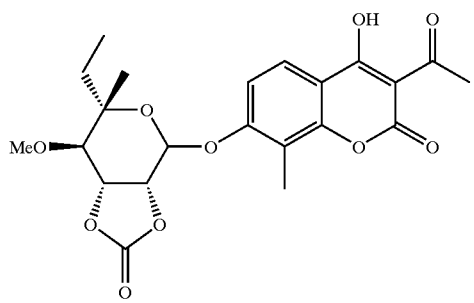

1.5 g of the product of the previous stage is dissolved in 15 ml of pyridine dried over potassium. 3.6 g of propargylhydroxylamine hydrochloride and 0.36 g of lithium perchlorate are added at ambient temperature. The reaction medium is agitated for 48 hours at ambient temperature followed by diluting with a heptane 1/ethyl acetate 2 mixture, and the organic phase is washed with a solution of sodium hydrogen sulphate at 10%, dried over magnesium sulphate.

1.8 g of sought product is obtained. 200 mg of this crude product is purified on silica with an eluent mixture methylene chloride 80/terbutylmethylether 20. 90 mg of sought product is obtained, isomer-3 and 75 mg of isomer-2. Yield: 77% 55/45 in isomer-3

STAGE F:

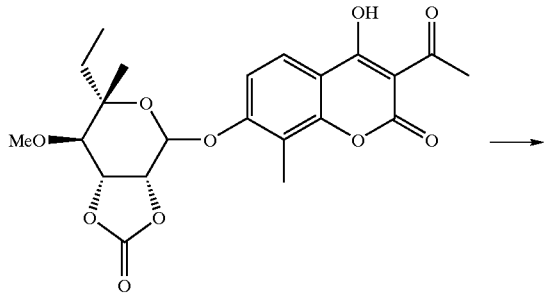

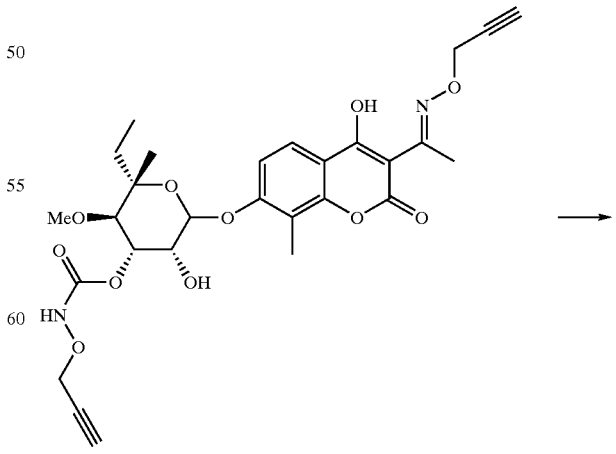

-continued

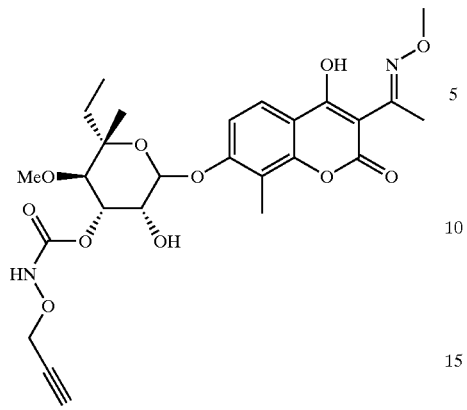

0.5 g of the product of the previous stage is dissolved in 5 ml of ethanol. 0.85 g of methylhydroxylamine hydrochloride and 0.94 g of potassium acetate are added at ambient temperature. The reaction medium is agitated for 5 hours at ambient temperature followed by diluting with a heptane 1/ethyl acetate 2 mixture, and the organic phase is washed with a 1 M sodium dihydrogen phosphate solution, dried over magnesium sulphate and evaporated to dryness. A crude product is obtained which is purified on silica with the eluent mixture methylene chloride with 20% of terbutylmethylether. 0.095 g of sought product is obtained.

STAGE G:

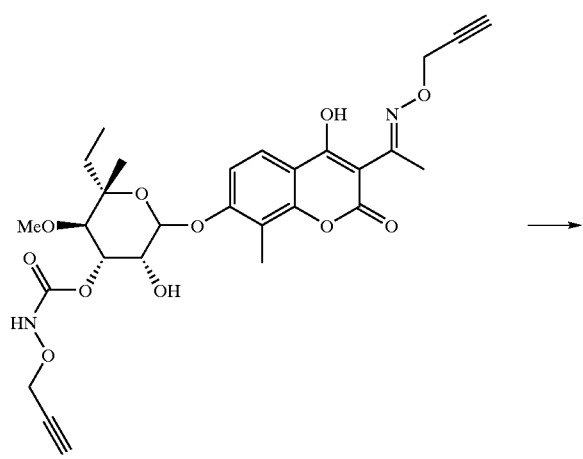

The operation is carried out as indicated in stage F using 0.85 g of ethyl hydroxylamine hydrochloride. 0.103 g of the expected product isomer-3 is obtained.

EXAMPLE 10

7-[(6-deoxy-5C-ethyl-4-O-methyl-.beta.-D-gulopyranosyl)oxy]-3-[1-(methoxy imino)propyl]-4-hydroxy-8-methyl-2H-1-benzopyran-2-one (2-propynyloxy)carbamic 3'-ester acid

STAGE A:

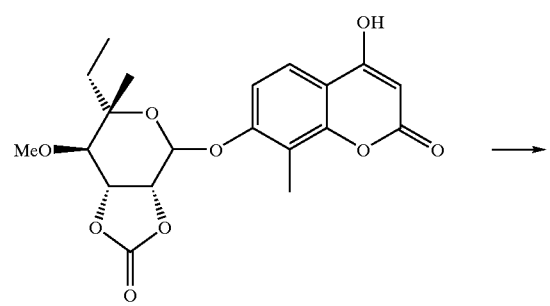

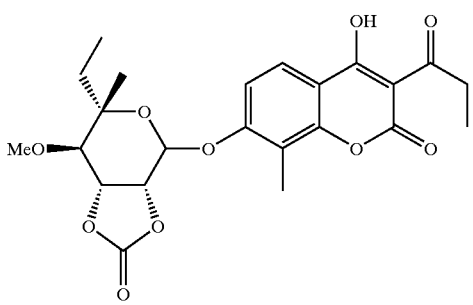

0.6 g of the product obtained as in stage C of Example 9 is dissolved in 15 ml of methylene chloride. 0.36 g of dimethylaminopyridine and dropwise, under argon at 0° C., 0.20 g of propionic anhydride are added. Agitation is carried out for 30 minutes at 0° C. then for 1 hour at ambient temperature. The reaction medium is diluted with 100 ml of heptane 1/ethyl acetate 2 mixture. The organic phase is washed with a 1 M aqueous sodium dihydrogen phosphate solution, dried over magnesium sulphate and evaporated to dryness. 0.6 g of sought product is obtained.

Yield: 68%

STAGE B:

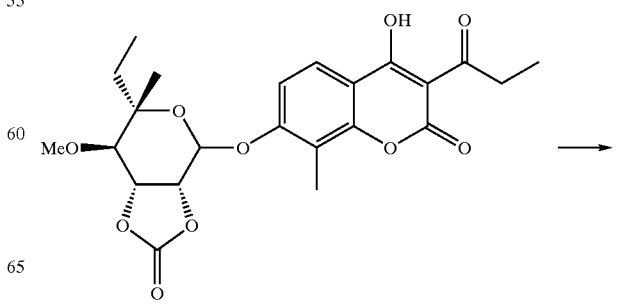

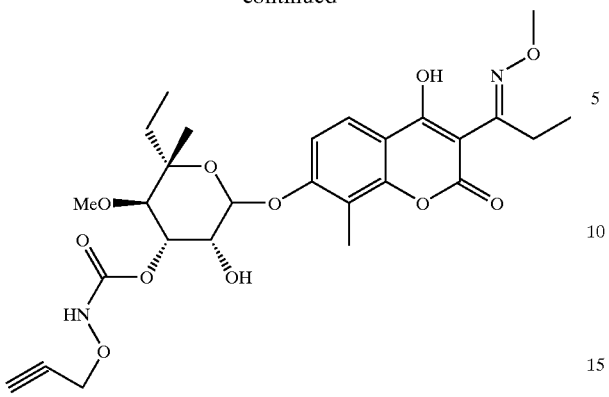

0.6 g of the product of the previous stage is dissolved in 6 ml of pyridine dried over potassium. 1.39 g of propargyl-hydroxylamine hydrochloride and 0.13 g of lithium perchlorate are added. The reaction medium is agitated for 48 hours at ambient temperature followed by diluting with a heptane 1/ethyl acetate 2 mixture and the organic phase is washed with a solution of sodium hydrogen sulphate at 10%, dried over magnesium sulphate.

0.56 g of product is obtained which is dissolved in 10 ml of ethanol, 1.07 g of methylhydroxylamine hydrochloride and 1.39 g of sodium acetate are added.

The reaction medium is agitated for 5 hours at ambient temperature followed by diluting with a heptane 1/ethyl acetate 2 mixture, and the organic phase is washed with a 1 M sodium dihydrogen phosphate solution, dried over magnesium sulphate and evaporated to dryness. 0.45 g of crude product is obtained which is purified by chromatography on silica eluting with a methylene chloride mixture with 20% of terbutylmethylether. 0.170 g of sought product is obtained.

Operating as previously, the products corresponding to the following formula were also prepared:

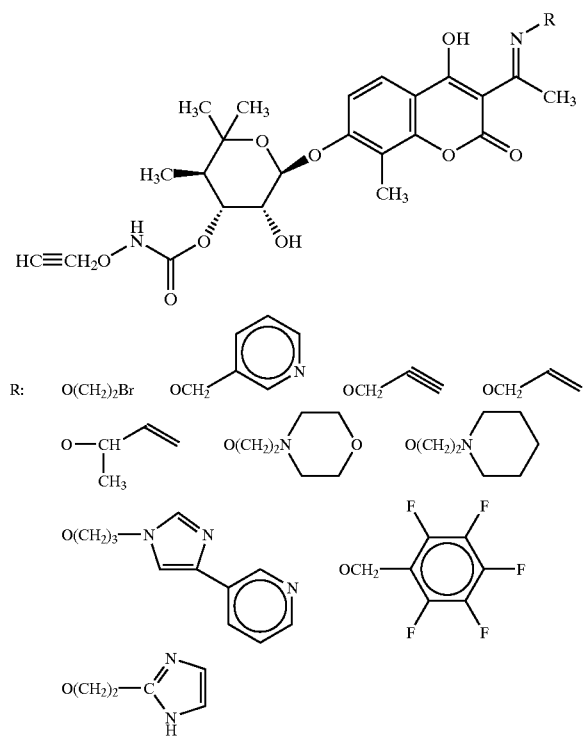

Operating as previously the following products corresponding to formula (I) were obtained:

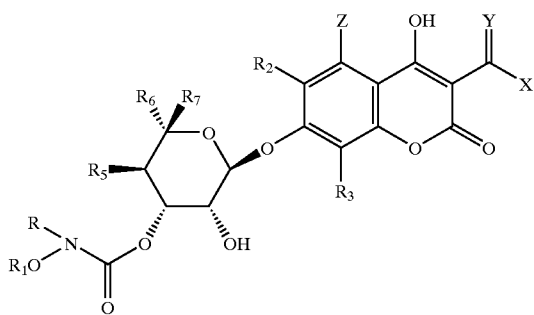

| $R_1$ | $R$ | $R_5$ | $R_6$ | $R_7$ | $R_2$ | $R_3$ | Z | Y | X |
|---|---|---|---|---|---|---|---|---|---|
| H | $CH_3$ | $OCH_3$ | $CH_3$ | $CH_3$ | H | $CH_3$ | H | O | $OC_2H_5$ |
| $CH_3$ | H | $OCH_3$ | $CH_3$ | $CH_3$ | H | $CH_3$ | H | O | $OC_2H_5$ |
| $C_2H_5$ | H | $OCH_3$ | $CH_3$ | $CH_3$ | H | $CH_3$ | H | O | $OC_2H_5$ |
| $C_2H_5$ | H | $OCH_3$ | $CH_3$ | $CH_3$ | H | $CH_3$ | H | O | $NH_2$ |
| $C_2H_5$ | H | $OCH_3$ | $CH_3$ | $CH_3$ | $H_3$ | H | $OCH_2Bz$ | O | $NH_2$ |
| $-CH_2-C=CH_2$ | H | $OCH_3$ | $CH_3$ | $CH_3$ | H | $CH_3$ | H | O | $OC_2H_5$ |
| $-CH_2-C=CH_2$ | H | $OCH_3$ | $CH_3$ | $CH_3$ | H | H | $OCH_2Bz$ | O | $NH_2$ |
| 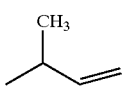 | H | $OCH_3$ | $CH_3$ | $CH_3$ | H | $CH_3$ | H | O | $OC_2H_5$ |

-continued

| R₁ | R | R₅ | R₆ | R₇ | R₂ | R₃ | Z | Y | X |
|---|---|---|---|---|---|---|---|---|---|
| CH₂=CHCH(CH₃)— (3-methylbut-1-en-3-yl) | H | OCH₃ | CH₃ | CH₃ | H | CH₃ | H | O | NH₂ |
| (CH₃)₂CHCH₂— (isobutyl) | H | OCH₃ | CH₃ | CH₃ | H | CH₃ | H | O | OC₂H₅ |
| —CH₂CH(CH₃)₂ | H | OCH₃ | CH₃ | CH₃ | H | CH₃ | H | O | NH₂ |
| —CH₂-cyclopropyl | H | OCH₃ | CH₃ | CH₃ | H | CH₃ | H | O | NH₂ |
| —CH₂-cyclopropyl | H | OCH₃ | CH₃ | CH₃ | H | CH₃ | OCH₂Bz | O | NH₂ |
| cyclopentyl | H | OCH₃ | CH₃ | CH₃ | H | CH₃ | H | O | CH₂CH₃ |
| cyclopentyl | H | OCH₃ | CH₃ | CH₃ | H | H | OCH₂Bz | O | NH₂ |
| cyclopentyl | H | OCH₃ | CH₃ | CH₃ | H | CH₃ | H | O | N—O-cyclopentyl |
| —CH₂—C≡CH | H | OCH₃ | CH₃ | CH₃ | H | CH₃ | H | O | CH₂ |
| —CH₂—C≡CH | H | OCH₃ | CH₃ | CH₃ | H | CH₃ | H | O | OC₂H₅ |
| —CH₂—C≡CH | H | OCH₃ | CH₃ | CH₃ | H | CH₃ | H | O | N(CH₂)₂NH₂ |
| —CH₂—C≡CH | H | OCH₃ | CH₃ | CH₃ | H | CH₃ | H | O | —NOCH₃ |
| HC≡C-CH(CH₃)— | H | OCH₃ | CH₃ | CH₃ | H | CH₃ | H | O | CH₃ |
| HC≡C-CH(CH₃)— | H | OCH₃ | CH₃ | CH₃ | H | CH₃ | H | NOCH₃ | OC₂H₅ |
| HC≡C-CH(CH₃)— | H | OCH₃ | CH₃ | CH₃ | H | CH₃ | H | O | OC₂H₅ |

-continued

| R₁ | R | R₅ | R₆ | R₇ | R₂ | R₃ | Z | Y | X |
|---|---|---|---|---|---|---|---|---|---|
| CH₃-CH(CH₃)-C≡CH (isopropyl-acetylene group, CH₃ branch) | H | OCH₃ | CH₃ | CH₃ | H | CH₃ | H | O | NH₂ |
| CH₃-CH(CH₃)-C≡CH | H | OCH₃ | CH₃ | CH₃ | H | CH₃ | H | O | N(CH₂)₂-piperazinyl-N |
| CH₃—C≡C—CH₂— | H | OCH₃ | CH₃ | CH₃ | H | CH₃ | H | O | OC₂H₅ |
| CH₃—C≡C—CH₂— | H | OCH₃ | CH₃ | CH₃ | H | CH₃ | H | O | NH₂ |
| NH≡C— | H | OCH₃ | CH₃ | CH₃ | H | CH₃ | H | O | OC₂H₅ |
| NH≡C— | H | OCH₃ | CH₃ | CH₃ | H | CH₃ | H | O | NH₂ |
| N≡C—(4-methylphenyl) | H | OCH₃ | CH₃ | CH₃ | H | CH₃ | H | O | N(CH₂)₂-morpholinyl-N |
| (4-methylphenyl) | H | OCH₃ | CH₃ | CH₃ | H | CH₃ | H | O | OC₂H₅ |
| ClCH₂—CH₂— | H | OCH₃ | CH₃ | CH₃ | H | CH₃ | H | O | OC₂H₅ |
| ClCH₂—CH₂— | H | OCH₃ | C₂H₅ | C₂H₅ | H | CH₃ | H | O | OC₂H₅ |

Operating as previously, the following products were prepared:

3-[1-[[(5-chloro-1,2,3-thiadiazol-4-yl)methoxy]imino]ethyl]-7-[(6-deoxy-5-C-methyl-4-O-methyl-.alpha.-L-lyxo-hexopyranosyl)oxy]-4-hydroxy-8-methyl-2H-1-benzopyran-2-one (2-propynyloxy)-carbamic 3'-ester acid 3-[1-[(cyanomethoxy)imino]ethyl]-7-[(6-deoxy-5-C-methyl-4-O-methyl-.alpha.-L-lyxo-hexopyranosyl)oxy]-4-hydroxy-8-methyl-2H-1-benzopyran-2-one (2-propynyloxy)-carbamic 3'-ester acid 3-[1-[(2-aminoethoxy)imino]ethyl]-7-[(6-deoxy-5-C-methyl-4-O-methyl-.alpha.-L-lyxo-hexopyranosyl)oxy]-4-hydroxy-8-methyl-2H-1-benzopyran-2-one (2-propynyloxy)-carbamic 3'-ester acid 7-[[6-deoxy-5-C-methyl-4-O-methyl-.alpha.-L-lyxo-hexopyranosyl)oxy]-4-hydroxy-8-methyl-3[1-[(2-hydroxyethoxy)imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[(3-piperidinyl)oxy]imino]ethyl]-2H-1-benzopyran-2-one (isomer B) (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[(3-piperidinyl)oxy]imino]ethyl]-2H-1-benzopyran-2-one (isomer A) (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[(1-methylethoxy)imino]ethyl]-2H-1-benzopyran-2-one (2-propynyloxy)-carbamic 3'-ester acid 3-[1-[(cycobutyloxy)imino]ethyl]-7-[(6-deoxy-5-C-methyl-4-O-methyl-.alpha.-L-lyxo-hexopyranosyl)oxy]-4-hydroxy-8-methyl-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-(propoxyimino)ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy)-4-hydroxy-8-methyl-3-[1-[2,2,2-trifluoroethoxy)imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[(pentafluorophenyl)methoxy]imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[3-[4-(3-pyridinyl)-1H-imidazol-1-yl]propoxy]imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[2-(1-piperidinyl)ethoxy]-imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[2-(4-morpholinyl)ethoxy]-imino]ethyl]-2H-1-benzopyran-2-one (2-propynyloxy)-carbamic 3,-ester acid 7-[(6-deoxy-5-C-methyl-4-O-methyl-.alpha.-L-lyxo-hexopyranosyl)oxy]-4-hydroxy-8-methyl-3-[1-(methoxyimino)propyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[(2,2,2-trifluoroethoxy)imino)propyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-(prppoxyimino)propyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy)-3-[1-(ethoxyimino)propyl]-4-hydroxy-8-methyl-2H-1-benzopyran-2-one (2-propynyloxy)-carbamic 3'-ester acid 7-[[6-deoxy-5-C-methyl-4-O-methyl-3-O-[[(2-propynyloxy)amino]carbonyl]-.alpha.-L-lyxo-hexopytanosyl)oxy]-3-(1-(ethoxymethoxy)imino]ethyl]-4-hydroxy-8-methyl-2H-1-benzopyran-2-one 7-([6-deoxy-5-C-methyl-4-O-methyl-3-O-[[(2-propynyloxy) propynyloxy)amino]carbonyl].alpha.-L-lyxo-hexopyranosyl)oxy]-4-hydroxy-8-methyl-3-[1-[[(2-methyl-4-thiazolyl)methoxy]imino]ethyl]-2H-1-benzopyran-2-one 7-[(6-deoxy-5-C-methyl-4-O-methyl-.alpha.-L-lyxo-hexopyranosyl)oxy]-4-hydroxy-8-methyl-3-[1-[[(2-thiazolyl)methoxy]imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-[[(3-furanyl)methoxy]imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-1-[1-[[(3-thienyl)methoxy)imino]ethyl]-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-3-[1-[[(2-furanylmethoxy)imino]ethyl]-8-methyl-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxyl-4-hydroxy-3-[1-[[(3,5-dimethyl-isoxazol-4-yl)methoxy]imino]ethyl]-8-methyl-2H-1-benzopyran-2-one (2-propynyloxy)-carbamic 3'-ester acid 7-[(6-deoxy-5-C-methyl-4-O-methyl-.alpha.-L-lyxo-hexopyranosyl)oxy]-4-hydroxy-8-methyl-3-[1-(phenoxyimino)ethyl]-2H-1-benzopyran-2-one (2-propynyloxy)-carbamic 3'-ester acid methyl [[[1-[7-[[6-deoxy-5-C-methyl-4-O-methyl-3-O-[[(2-propynyloxy)amino]carbonyl]-.alpha.-L-lyxo-hexopyranosyl)oxy]3-4-hydroxy-8-methyl-2-oxo-2H-1-benzopyran-3-yl]ethylidene]amino]oxy]acetate Examples of Pharmaceutical Compositions Tablets were prepared containing:

Product of Example 1 150 mg

Excipient s.g.t. 1 g

Detail of excipient: starch, talc, magnesium stearate

Product of Example 5 150 mg

Excipient s.g.t. 1 g

Detail of excipient: starch, talc, magnesium stearate

Injectable solutions were also prepared from salified products.

Pharmacological Study of the Products of the Invention

A—Method of Dilutions in Liquid Medium

A series of tubes is prepared in which the same quantity of sterile nutritive medium is distributed. Increasin quantities of the product to be studied are distributed into each tube, then each tube is sown with a bacterial strain. After incubation for twenty-four hours in an oven at 37° C., the growth inhibition is evaluated by transillumination, which allows the minimal inhibitory concentrations (M.I.C.) to be determined, expressed in micrograms/cm$^3$.

Activity in vitro

MIC in µg/ml

On the following strains:

|  | EX. 1 | Ex. 2 | Ex. 3 | Ex. 4 |
|---|---|---|---|---|
| Staph. aureus 011HT18 | 0.04 | 0.04 | 0.04 | 0.04 |
| Staph. epidermidis 0126042 | 0.04 | 0.04 | 0.04 | 0.15 |
| Staph. coag. negative 012HT5 | 0.3 | 0.04 | 0.15 | 0.15 |
| Strepto. pyogene 02A1UCl | 0.6 | 0.3 | 0.6 | 0.6 |
| Strepto. pneumoniae 030BI2 | 0.04 | 0.08 | 0.08 | 0.15 |
| Entero faecium 02D3IP2 | 0.08 | 0.6 | 1.2 | 1.2 |
| Entero faecalis 02D2UC5 | 0.3 | 1.2 | 1.2 | 1.2 |

B—Inhibition of gyrase B

The products are inhibitors of gyrase B; the dose at 50% of DNA supercoiling is less than 5 µg/ml.

What is claimed is:

1. A compound selected from the group consisting of a compound of the formula

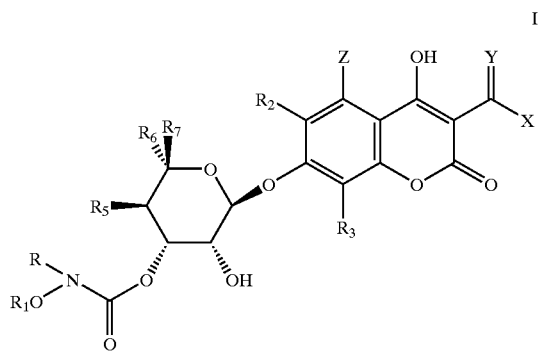

I wherein Y is selected from the group consiting of oxygen, =N-Nalk, and =Noalk$_2$, alk$_1$ and alk$_2$ are individually alkyl of 1 to 12 carbon atoms optionally interrupted by at least one member of the group consisting of oxygen, sulfur and nitrogen and optionally substituted with at least one member of the group consisting of halogen, aryl, haloaryl, heterocyclic and

Ra and Rb are individually hydrogen or substituted or unsubstituted alkyl of 1 to 8 carbon atoms or Ra and Rb with the nitrogen to which they are attached form a heterocycle which may contain another hetero atom selected from the group consisting of oxygen, sulfur and nitrogen, X is selected from the group consisting of hydrogen, —OH, linear, branched or cyclic alkyl, alkenyl and alkynyl of up to 12 carbon atom's optionally interrupted by at least one member of the group consisting of oxygen, nitrogen and sulfur, optionally substituted by at least one member of the group consisting of halogen, heterocycle, —OH, acyloxy, —CN, —NO$_2$,

wherein Ra and Rb are defined as above, alkoxy of up to 12 carbon atoms,

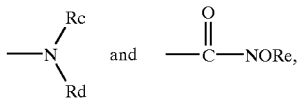

wherein Rc and Rd have the definition of Ra and Rb, Re is alkyl of 1 to 8 carbon atoms unsubstituted or substituted as above, Z is selected from the group consisting of hydrogen, halogen and —OH free or esterified or etherified, R$_2$ is hydrogen or halogen, R$_3$ is selected from the group consisting of hydrogen, halogen and alkyl of 1 to 8 carbon atoms, R is hydrogen or alkyl of 1 to 4 carbon atoms, R$_1$ is selected from the group consisting of hydrogen, —CN, aryl of 6 to 14 carbon atoms and alkyl, cycloalkyl, alkenyl and alkynyl of up to 8 carbon atoms unsubstituted or substituted with at least one halogen, R$_5$ is hydrogen or alkoxy of 1 to 4 carbon atoms, R$_6$ is alkenyl of 2 to 3 carbon atoms and R$_7$ is hydrogen or alkyl of 1 to 8 carbon atoms and its non-toxic, pharmaceutically acceptable acid addition salts.

2. A compound of claim 1 wherein Y is oxygen.
3. A compound of claim 1 wherein Y is NO-alkyl 1 to 4 carbon atoms.
4. A compound of claim 1 wherein Y is —NOC$_2$H$_5$.
5. A compound of claim 1 wherein X is alkyl of 1 to 4 carbon atoms.
6. A compound of claim 1 wherein X is —NH$_2$.
7. A compound of claim 1 wherein X is

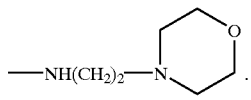

8. A compound of claim 1 wherein R$_1$ is:

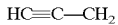

9. A compound of claim 1 wherein R is hydrogen.
10. A compound of claim 1 wherein R$_3$ is methyl.
11. A compound of claim 1 wherein Z is hydrogen.
12. A compound of claim 1 wherein R$_2$ is hydrogen.
13. A compound of claim 1 wherein R$_5$ is OCH$_3$.
14. A compound of claim 1 wherein R$_6$ is ethenyl.
15. A compound of claim 1 wherein R$_7$ is ethyl.
16. A compound of claim 1 wherein, R$_6$ is propenyl.
17. A method of treating bacterial infections in warm-blooded animals comprising administering to warm-blooded animals in need thereof a bactericidally effective amount of a compound of claim 1.

* * * * *